US008180442B2

(12) United States Patent
Belalcazar et al.

(10) Patent No.: US 8,180,442 B2
(45) Date of Patent: May 15, 2012

(54) DERIVING PATIENT ACTIVITY INFORMATION FROM SENSED BODY ELECTRICAL INFORMATION

(75) Inventors: Andres Belalcazar, Saint Paul, MN (US); Ji Chen, Woodbury, MN (US)

(73) Assignee: Greatbatch Ltd., Clarence, NY (US)

( * ) Notice: Subject to any disclaimer, the term of this patent is extended or adjusted under 35 U.S.C. 154(b) by 1062 days.

(21) Appl. No.: 11/956,884

(22) Filed: Dec. 14, 2007

(65) Prior Publication Data

US 2009/0156908 A1 Jun. 18, 2009

(51) Int. Cl.
*A61B 5/04* (2006.01)

(52) U.S. Cl. ......................... 600/546; 600/547

(58) Field of Classification Search .................. 600/546, 600/547
See application file for complete search history.

(56) References Cited

U.S. PATENT DOCUMENTS

| 5,113,859 | A | 5/1992 | Funke |
| 6,097,983 | A * | 8/2000 | Strandberg ........................ 607/9 |
| 6,236,882 | B1 | 5/2001 | Lee et al. |
| 6,317,625 | B1 | 11/2001 | Olson et al. |
| 6,347,245 | B1 | 2/2002 | Lee et al. |
| 6,471,645 | B1 | 10/2002 | Warkentin et al. |
| 6,625,493 | B2 | 9/2003 | Kroll et al. |
| 6,658,292 | B2 | 12/2003 | Kroll et al. |
| 6,824,512 | B2 | 11/2004 | Warkentin et al. |
| 7,016,721 | B2 | 3/2006 | Lee et al. |
| 7,076,301 | B1 | 7/2006 | Kroll et al. |
| 7,189,204 | B2 | 3/2007 | Ni et al. |
| 2002/0026122 | A1 | 2/2002 | Lee et al. |
| 2002/0111542 | A1 | 8/2002 | Warkentin et al. |
| 2003/0040776 | A1 | 2/2003 | Kroll et al. |
| 2003/0040778 | A1 | 2/2003 | Kroll et al. |
| 2004/0077995 | A1 | 4/2004 | Ferek-Petric et al. |
| 2004/0111040 | A1 | 6/2004 | Ni et al. |
| 2004/0111041 | A1 | 6/2004 | Ni et al. |
| 2004/0152957 | A1 * | 8/2004 | Stivoric et al. ................ 600/300 |
| 2004/0220633 | A1 * | 11/2004 | Wagner et al. ..................... 607/9 |
| 2005/0042589 | A1 | 2/2005 | Hatlestad et al. |
| 2005/0043652 | A1 | 2/2005 | Lovett et al. |
| 2005/0061315 | A1 | 3/2005 | Lee et al. |
| 2005/0070971 | A1 | 3/2005 | Fowler et al. |

(Continued)

OTHER PUBLICATIONS

'Normal ECG' [online]. HealthyHearts, [retrieved on Jul. 3, 2007]. Retrieved from the Internet: <URL: http://www.healthyhearts.com/ecg/normalecg/htm>, 3 pages.

(Continued)

*Primary Examiner* — Carl H Layno
*Assistant Examiner* — Natasha Patel
(74) *Attorney, Agent, or Firm* — Michael F. Scalise; Fish & Richardson P.C.

(57) ABSTRACT

Electrodes of a subcutaneous monitoring system receive body electrical signals that indicate both cardiac and non-cardiac muscle activity. In general, non-cardiac muscle activity is often correlated with physical activity, and physical activity is typically a strong indicator of patient health. Exemplary systems and methods that detect non-cardiac muscle activity information in sensed body electrical waveforms may provide a diagnostic tool for monitoring physical activity level over time in patients that have subcutaneous monitoring systems. In an illustrative embodiment, systems and methods for presenting patient activity information in a graphical format over intervals of time include processing ECG waveform information to identify and to accumulate non-cardiac muscular activity information during each of the intervals of time. In various implementations, number, intensity, and/or duration of the events that are identified during a time interval may be accumulated and stored for subsequent recall.

17 Claims, 12 Drawing Sheets

U.S. PATENT DOCUMENTS

| | | |
|---|---|---|
| 2005/0074741 A1 | 4/2005 | Lee et al. |
| 2005/0076908 A1 | 4/2005 | Lee et al. |
| 2005/0107838 A1 | 5/2005 | Lovett et al. |
| 2005/0115561 A1 | 6/2005 | Stahmann et al. |
| 2005/0165457 A1 | 7/2005 | Benser et al. |
| 2005/0177097 A1 | 8/2005 | Hildebrand et al. |
| 2005/0177135 A1 | 8/2005 | Hildebrand et al. |
| 2005/0197588 A1 | 9/2005 | Freeberg |
| 2005/0209511 A1 | 9/2005 | Heruth et al. |
| 2005/0209513 A1 | 9/2005 | Heruth et al. |
| 2005/0209643 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0234518 A1 | 10/2005 | Heruth et al. |
| 2005/0245971 A1 | 11/2005 | Brockway et al. |
| 2006/0116593 A1 | 6/2006 | Zhang et al. |
| 2006/0190056 A1 | 8/2006 | Fowler et al. |
| 2006/0195149 A1 | 8/2006 | Hopper et al. |
| 2006/0206066 A1 | 9/2006 | Ferek-Petric |
| 2006/0206067 A1 | 9/2006 | Ferek-Petric |
| 2006/0235472 A1 | 10/2006 | Goetz et al. |
| 2006/0253043 A1 | 11/2006 | Zhang et al. |
| 2006/0253044 A1 | 11/2006 | Zhang et al. |
| 2006/0253164 A1 | 11/2006 | Zhang et al. |
| 2007/0032733 A1 | 2/2007 | Burton |
| 2007/0118180 A1 | 5/2007 | Ni et al. |

OTHER PUBLICATIONS

Virtuoso ICD—Cardiac Compass Trends [online]. Medtronic, Inc., 2006, [retrieved on Dec. 13, 2007]. Retrieved from the Internet: <URL: http://www.medtronic.com/physician/tachy/icd/compass_trends.pdf>, 4 pages.

'Cardiac Compass Trends—Using Pacemaker Monitoring to Facilitate AF Management' [online]. Medtronic, 2003, [retrieved on Dec. 13, 2007]. Retrieved from the Internet: <URL: http://www.optimalpacing.com/long-term-surveillance/solutions/CardiacCompassAFMgmt.pdf>, 4 pages.

Kadhiresan et al., "A Novel Method—The Activity Log Index—for Monitoring Physical Activity of Patients With Heart Failure," *The American Journal of Cardiology*, Jun. 15, 2002, 89(12): 1435-1437..

\* cited by examiner

Active Patient

Sedentary Patient

DERIVING PATIENT ACTIVITY INFORMATION FROM SENSED BODY ELECTRICAL INFORMATION

TECHNICAL FIELD

Various embodiments relate to monitoring a patient's physical activity based on body electrical information sensed by electrodes within a body of the patient.

BACKGROUND

Electrical signals cause a heart to beat. In a healthy patient, regular heart beats pump blood through the cardiovascular system. The human cardiovascular system is responsible for receiving oxygen-deprived blood into the heart from the venous system of the body, delivering the oxygen-deprived blood to the lungs to be replenished with oxygen, receiving the oxygenated blood from the lungs back into the heart, and delivering the oxygenated blood to the body via the arterial vasculature. This process is regulated within the heart by electrical pulses that control operation of the heart's receiving and pumping chambers.

In a healthy heart, the sinoatrial node of the heart generates electrical pulses in a consistent and regulated fashion to regulate receiving and pumping blood in the heart's chambers. The electrical impulses propagate as activation wavefronts across the atria, the upper chambers of the heart, and cause cells of the atria to depolarize and contract, which forces blood from the atria to the ventricles, the lower chambers of the heart. The ventricles receive the blood from the atria, and the wavefront, after passing through the atrioventricular node and moving to the Purkinje system, moves to cells of the ventricles causing the ventricles to contract and pump the blood to the lungs and to the rest of the body.

Various aspects of cardiac activity (e.g., heart rate, arrhythmias) can be detected by measuring, recording, and analyzing cardiac electrical signals, such as an electrocardiogram (ECG) signal. One way of measuring ECG signals involves attaching electrodes, typically ten, externally to a patient's skin and sensing the electrical signals that form the ECG waveform.

Implantable monitoring systems can be implanted under the skin with electrodes that sense subcutaneous electrical signals, including ECG signals, which are analyzed as being indicative of cardiac activity. In such systems, the electrodes also receive extraneous non-cardiac electrical signal information, which is typically filtered out to produce a more readable ECG. Non-cardiac electrical signals can be generated by muscle tissues during physical activity.

SUMMARY

Electrodes of a subcutaneous monitoring system receive body electrical signals that indicate both cardiac and non-cardiac muscle activity. In general, non-cardiac muscle activity is often correlated with physical activity, and physical activity is typically a strong indicator of patient health. Exemplary systems and methods that detect non-cardiac muscle activity information in ECG waveforms may give health care providers a diagnostic tool for monitoring physical activity level over time in patients that have subcutaneous monitoring systems.

Various embodiments monitor a patient's activity level over time by processing received ECG signals to detect episodes of electrical signals that indicate non-cardiac activity. In some examples, systems and methods for presenting patient activity information in a graphical format over intervals of time include processing ECG waveform information to identify and to accumulate non-cardiac muscular activity information during each of the intervals of time. In an illustrative embodiment, ECG waveforms received by subcutaneous electrodes may be processed by analog and/or digital signal processing techniques to identify signals indicative of non-cardiac muscle activity. In various implementations, number, intensity, and/or duration of the events that are identified during a time interval may be accumulated and stored for subsequent recall. In an illustrative diagnostic application, the accumulated information may graphically represent patient activity levels during each of a number of selected time intervals to a reviewing health care provider.

Some embodiments may have one or more advantages. For example, some embodiments may take advantage of existing ECG waveform detection capability of existing implanted devices, for example, with or without the addition of a software modification to the implanted medical device. In particular embodiments, telemetered ECG waveform information may be processed digitally to detect and/or characterize non-cardiac muscle electrical noise (e.g., EMG) events. Various embodiments may further process for display the patient activity information according to configurable parameters, such as number of events within each of a number of user-specified time intervals, event duration, event intensity, and/or a combination of these or other parameters, such as integration over time of non-cardiac muscle activity. Some embodiments may further include improved sensitivity to non-cardiac muscle activity, for example, by substantially removing a coating, which may be applied to conductive exterior portions of an implantable medical device, to provide more direct electrical interface between implanted electrodes (e.g., a housing or "can" of the implantable device) and non-cardiac muscle tissues (e.g., fascia of the muscles).

Various embodiments may provide significantly improved quality and flexibility in the presentation of patient activity information to medical personnel. Various implementations may provide graphical display of patient information, for example, on demand or in substantially real time. Various parameters, such as interval length, number, and/or spacing, display formatting may be independently controllable, such as by automatic detection of the size and/or contents of the data set to be displayed in combination with optional user override capability. Various implementations may afford improved flexibility in component capabilities within the overall system architecture, for example by post-processing ECG waveform data, in whole or in part, at any of the nodes in the system network. Thus, data storage and processing operations performed within the system may be dynamically reconfigured to optimize performance. By way of example, post-processing may occur, at least in part, in a medical device implanted within the patient, at a communication node local to the patient, at a central data center, and/or at a remote client device operated by medical personnel reviewing the patient activity information in desired time ranges of interest.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION OF ILLUSTRATIVE EXAMPLES

When diagnosing or counseling a patient, medical care providers often would like to have accurate information about the patient's level of physical activity. Physical activity level, such as whether the patient is generally sedentary or highly active, can sometimes give valuable insight about the patient's overall health. For example, information about physical activity levels at night may shed light on the quality of the patient's sleep, and information about physical activity levels during waking hours may shed light on the quality of exercise or stress level for that patient.

Physical activity information may be valuable not only in accurately diagnosing health issues, but also in prescribing an appropriate treatment. In an illustrative example, a relatively small subdermal body electrical signal sensor system is implanted to temporarily monitor body electrical signals. If the monitored body signals include ECG signals, the ECG signals may be evaluated (e.g., to detect arrhythmias) to make a diagnosis of cardiac arrhythmias, or to determine whether the patient is a good candidate for an implantable medical device, such as a pacemaker, cardioverter-defibrillator, or other cardiac rhythm management device. The collected ECG information may also pick up important transient events that are unlikely to be detected without continuous monitoring over a period of time. After evaluating the ECG data collected over a period of time, an appropriate treatment plan may be designed by the medical care team. For example, a cardiologist may determine what type of implantable medical device to use, and how best to apply it (e.g., where to apply the electrodes to stimulate the heart, criteria for initiating and parameters for delivering electrical stimulation) to meet the needs of the patient. With the addition of some hardware and/or software to the ECG sensor system, the acquired ECG information can further be evaluated to identify physical activity level over time. When considered together, ECG and physical activity information provide a substantially more complete picture of the health of the patient than either ECG or physical activity information taken alone. In particular, features of the ECG may be explained or better understood after correlation with contemporaneous patient activity measurements. For example, ECG features may be determined to have occurred during sleep or after vigorous physical exercise, and thus the ECG features may be evaluated in the context of the physical activity information.

Figure 1A:
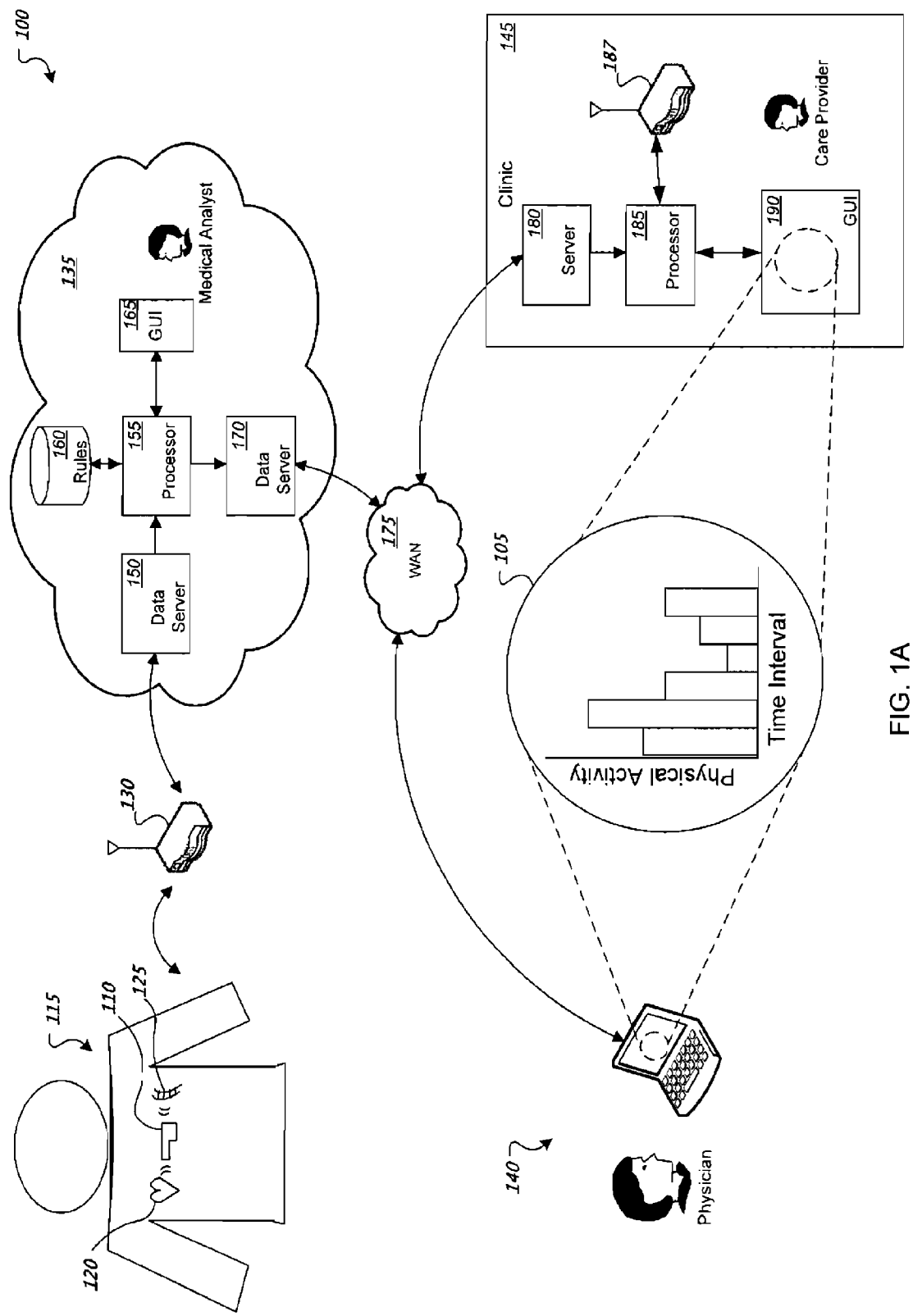
FIG. 1A shows an exemplary system to acquire ECG waveform data, to process the ECG waveform to identify non-cardiac muscle activity in each of a number of time intervals, and to use the identified non-cardiac muscle activity to display a graphical representation of patient activity in each of the time intervals.

FIG. 1A shows an exemplary system 100 to acquire ECG waveform data, to process the ECG waveform to identify non-cardiac muscle activity in each of a number of time intervals, and to present the identified non-cardiac muscle activity information in a graphical representation 105 of patient activity in each of the time intervals.

In one embodiment, the graphical representation 105 includes a histogram representing the number of non-cardiac muscle activity events that were identified in a portion of an ECG waveform. In an illustrative example, a histogram may graphically present, for each of a number of time intervals, a tally of the number of non-cardiac muscle activity events detected in a portion of an ECG waveform acquired during the corresponding time interval. In some embodiments, the graphical representation further illustrates intensity and/or duration of non-cardiac muscle activity during each time interval. Health care providers may advantageously review such graphical representations, and "at a glance" diagnose trends or status of the level and/or quality of patient activity, which can be a significant indicator of patient health. Furthermore, patient activity levels may be advantageously monitored in substantially real time or near real time, and the system 100 may automatically generate various levels of warning or notification messages to alert remote medical personnel and/or the patient if patient activity levels fall outside of certain predetermined ranges.

The exemplary system 100 includes a medical device 110 implanted within a body of a patient 115. The medical device 110 has at least two (e.g., three or four or more) subcutaneous electrodes configured for sensing ECG waveforms associated with electrical activity of the patient's heart 120. In some examples, at least one of the subcutaneous electrodes is positioned substantially in or around the heart 120 to increase sensitivity to electrical signals associated with cardiac muscle activity. In some examples, one electrode of the medical device 110 is disposed on a housing (e.g., "can") of the device 110.

Also within the patient's 115 body are non-cardiac muscle tissues 125. By way of example, and not limitation, non-cardiac muscle tissues 125 may include muscle and/or fascia tissues in and around the chest (e.g., pectorals), abdomen, back, or neck regions. During patient activity (e.g., exercise, lifting, arm movements, and the like), the electrodes of the medical device 110 may receive electrical signals associated with activity in the non-cardiac muscle tissue 125 as well as electrical signals associated with activity of the heart 120. As such, signals for the non-cardiac muscle activity combine with (e.g., add to) the ECG waveform signals associated with pumping of the heart 120. The absence of non-cardiac muscle signals generally indicates a corresponding absence of physical activity.

In one illustrative example, the medical device 110 receives an electrical waveform with a combination of cardiac signals associated with the heart 120 and non-cardiac muscle activity signals associated with the non-cardiac muscle tissues 125. At one or more points in the system 100, processing is performed to detect non-cardiac muscle activity events that may be indicated by the non-cardiac portions of the combined waveform.

The system 100 also includes an exemplary local communication module 130 that is local to the patient 115 and configured to communicate with the medical device 110 over a transdermal wireless link. In the depicted example, the module 130 performs a repeater function to support a further communication link to a remote data processing facility 135, for example. In some embodiments, the module 130 also performs operations to detect non-cardiac muscle activity events. Such detection operations may be performed automatically, or in response to a request or predetermined schedule, for example, from a system operator, medical personnel, or the patient 115. The processing may include analog and/or digital signal processing, depending on whether the information is received from the device 110 in analog (e.g., continuous waveform signal) or digital (e.g., sampled data) format.

The exemplary remote data processing facility 135 of the system 100 provides data processing, storage, analysis, monitoring, and distribution to remote medical personnel, such as a physician's remote access node 140 and a medical clinic 145.

As an illustrative example, a data server 150 at the remote data processing facility may receive over the Internet secure (e.g., encrypted) data packets that contain ECG waveform information from the local communication module 130 located in another country. To the extent the received information requires further processing to detect and/or characterize the occurrences, intensities (e.g., amplitudes), and/or durations over one or more selected thresholds of non-cardiac muscle activity, a processor 155 performs suitable analog and/or digital signal processing on the received information. Examples of such processing are further described with reference to FIG. 4B. The processor 155 compares the resulting processed data, which represents activity level information about the patient 115, to a rules database 160. The exemplary rules database 160 contains, for example, one or more predetermined conditions that, if met by the activity level information, trigger a notification message to a graphic user interface 165 (GUI) being monitored by a medical analyst, the physician at the remote access node 140, and/or a care provider at the clinic 145. In some examples, a notification message or action may include automatically attempting to contact the patient 115 by phone, or even dispatching emergency personnel (e.g., by ambulance). A medical analyst may monitor trends in patient activity levels, and manually watch for abnormal conditions that indicate the need for attention from medical personnel. The medical analyst may, for example, update the rules database 160 to set conditions and notification/action responses under the direction of the medical team responsible for the patient 115.

The remote data processing facility 135 further includes a data server 170 that provides for communication between the facility 135, the remote access node 140, and the clinic 145. The notification messages generated in response to abnormal activity level information are sent from the data server 170 to an exemplary wide area network 175 (WAN). The WAN 175 enhances the flexibility to communicate diagnostic patient activity level information with, for example, specialized health care providers who are at remote locations. In an illustrative example, current and historical patient activity level information may be sent via the WAN 175 for display in the form of the graphical representation 105 that is rendered on a display device being monitored by a physician at the remote access node 140. The display device may include a color screen as part of, for example, a laptop computer with a wired network connection to the WAN 175, or a handheld personal communication device with wireless connection to the WAN 175 to enable data exchanges with the remote data processing facility 135.

The clinic 145 includes a server 180 for communication of raw ECG data, partially processed muscle activity information, and/or fully processed activity information. Information received by the server 180 is processed by the processor 185. In some examples, the processor 185 may perform digital and/or analog signal processing to identify and/or characterize the number, intensity, and/or duration of non-cardiac muscle activity events during a number of time intervals, which time intervals may be specified, for example, by a health care provider. The clinic 145 further includes a local communication module 187 that is configured to communicate with the medical device 110 over a transdermal wireless link when the patient 115 is at the clinic 145. The processor 185 can directly send commands to the medical device 110, and receive ECG waveform data directly via the local communication module 187. In some embodiments, the local communication module 187 may have certain features (e.g., programming, diagnostic) capabilities enabled that are not enabled in a similar module (e.g., the local communication module 130 located in a home of the patient 115) that is outside of the health care provider's direct control.

In an illustrative example, a care provider may operate the GUI 190 to select or specify parameters for processing and/or displaying non-cardiac muscle activity information. For example, the user may specify that the GUI 190 display non-cardiac patient activity information in two-dimensional or three-dimensional formats, examples of which are described with reference to FIGS. 2A-2E.

Figure 1B:
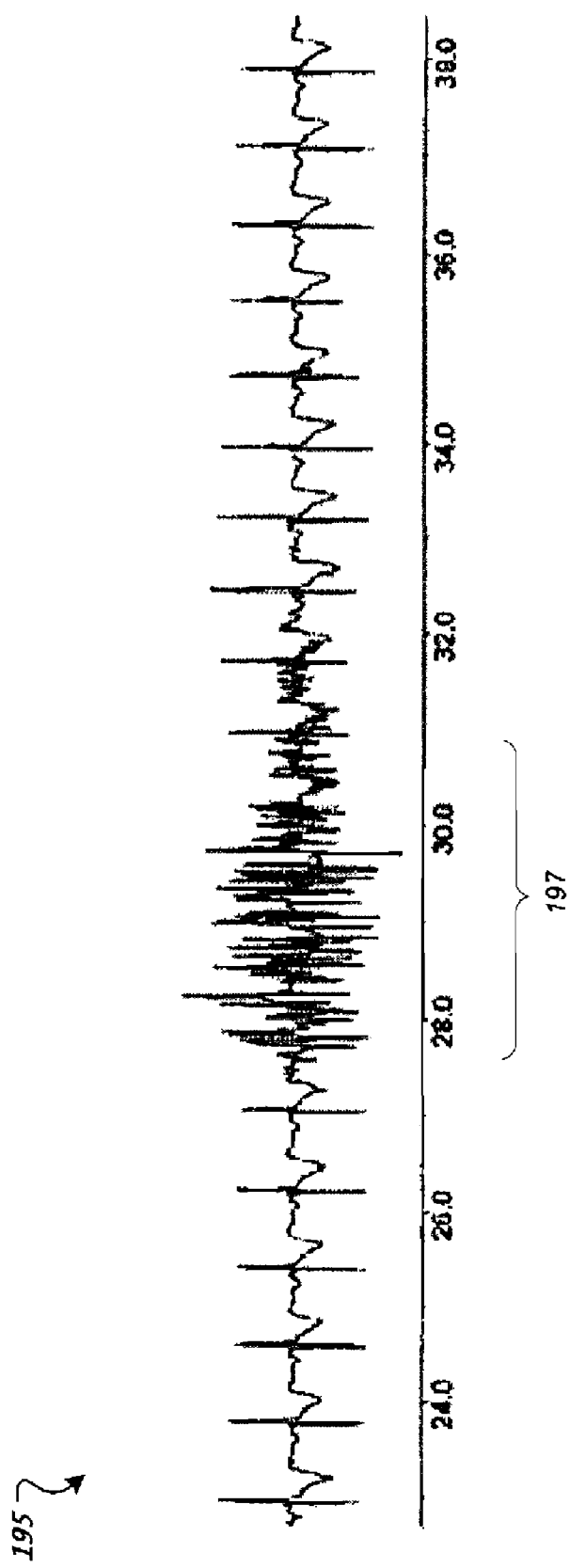
FIG. 1B illustrates a typical example of an ECG waveform acquired by a subcutaneous cardiac rhythm monitoring device.

FIG. 1B illustrates a typical example of an ECG waveform 195 acquired by a subcutaneous cardiac rhythm monitoring device. The ECG waveform 195 includes a combination of electrical signals associated with activity in the non-cardiac muscle tissue 125 superimposed with electrical signals associated with activity of the heart 120. The electrical signals associated with activity of the heart 120 appear as a substantially repeating series of QRS complex signals. Signals associated with non-cardiac muscle activity appear as an episode 197 of relatively higher frequency signals superimposed on the repeating cardiac waveforms.

In various examples, the system 100 operates to acquire the ECG waveform 195 using subcutaneous electrodes, processes the ECG waveform 195 to identify episodes of non-cardiac muscle activity, such as the episode 197, accumulate information about the identified episodes that occur during specified time intervals, and formats the accumulated information for display in the graphical representation 105. In various examples, the accumulated information may include an aggregate of the number of episodes that occur during the specified time interval, the intensity (e.g., peak or average amplitude), an accumulated or average duration of the episode (e.g., time that the episode satisfies a minimum threshold intensity), and/or an integration of the intensity of each event over time. Various examples may be displayed in a two- or three-dimensional histogram or trend type graphical representation.

FIGS. 2A-2E show some illustrative examples of two- or three-dimensional histogram-type graphical representations to present the accumulated physical activity information during each of a number of specified time intervals. Such graphical presentations, such as the graphical presentation 105, may facilitate rapid "at a glance" review of physical activity levels or trends, which are sometimes key diagnostic indicators of patient health, by a physician or other health care personnel, for example.

Figure 2A:
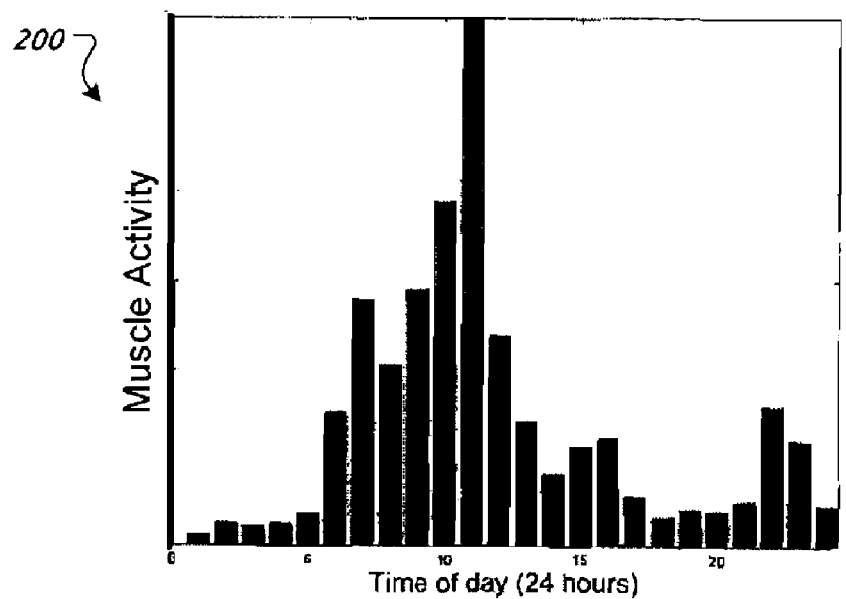
FIGS. 2A-2E show some illustrative examples of two- or three-dimensional histogram-type graphical representations to present the accumulated physical activity information during each of a number of specified time intervals.
Figure 2B:
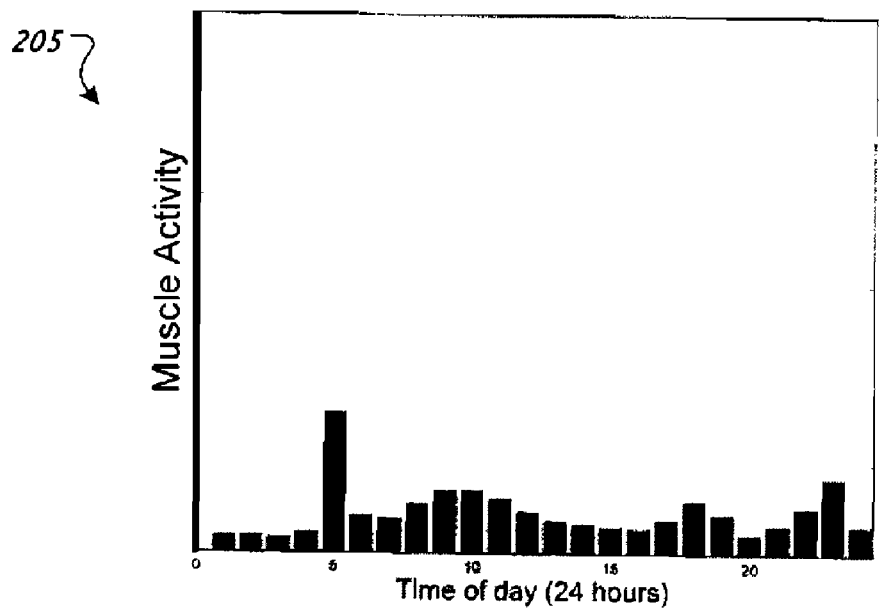

FIGS. 2A-2B show exemplary two dimensional graphical representations 200, 205, for an active patient and a sedentary patient, respectively. The vertical axes of both graphs 200, 205 represent an average rate at which non-cardiac muscle activity signals in a patient's ECG waveform exceeded minimum threshold detection criteria. In this example, the active patient had significantly higher rates of non-cardiac muscle activity than the sedentary patient had during the middle hours of the day. Both patients had similar rates during some of the early morning hours corresponding to sleep times.

Figure 2C:
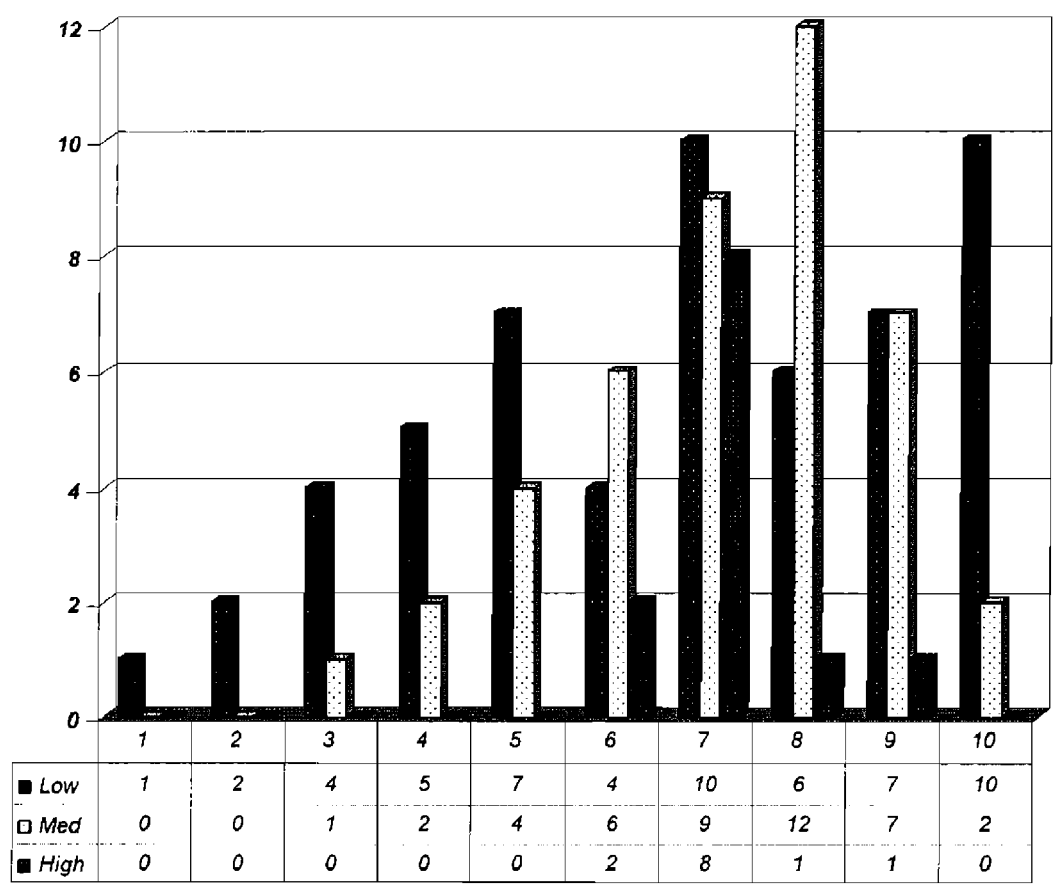
Figure 2D:
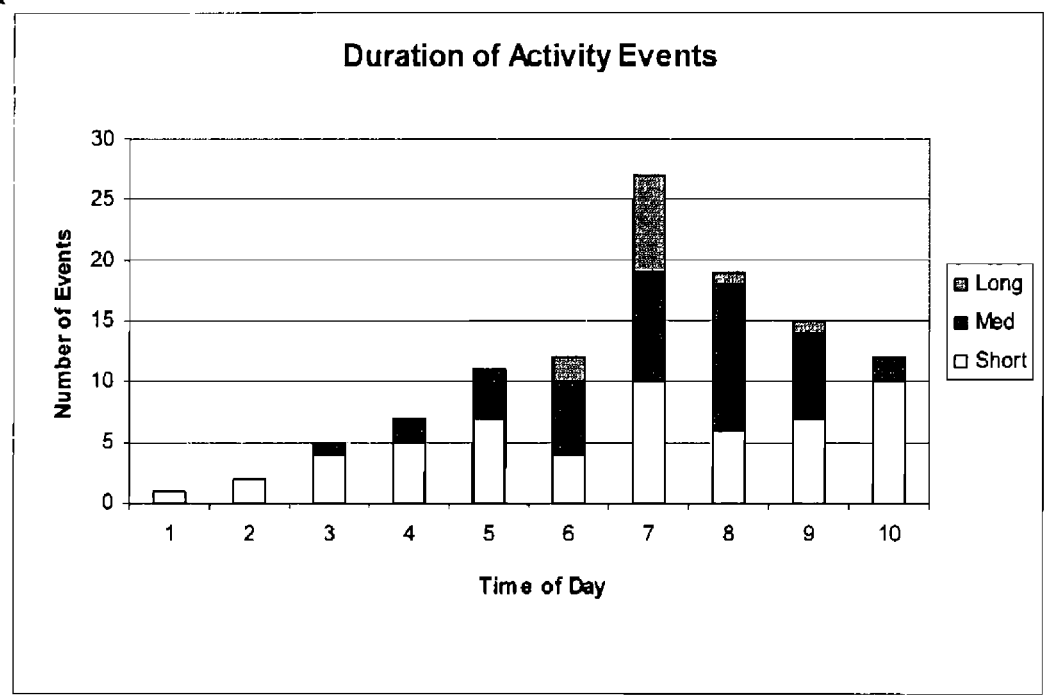
Figure 2E:
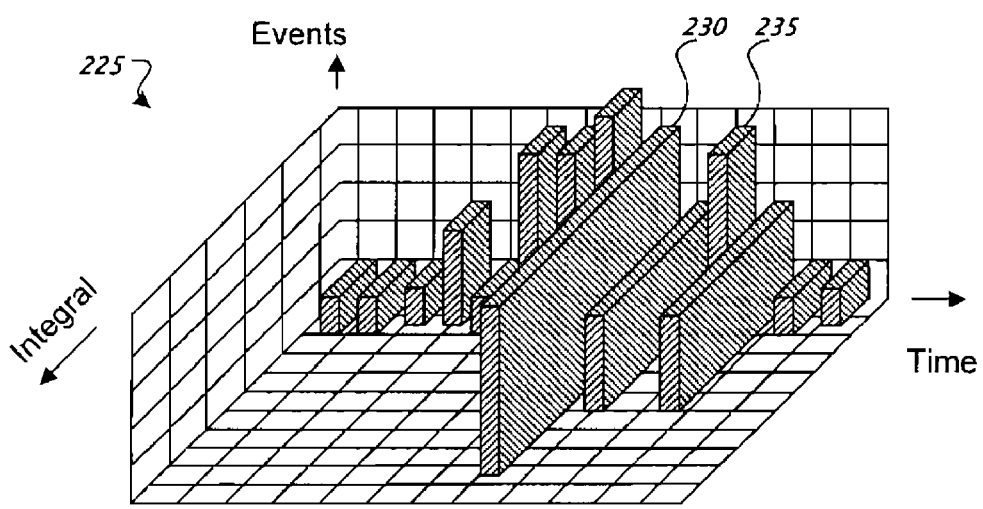

FIGS. 2C-2E show exemplary graphical representations that provide information about both the quantity (e.g., number of events detected in each time interval) and the quality (e.g., intensity and/or duration) of the patient's activity as derived from non-cardiac signals detected in an ECG waveform.

FIG. 2C shows an exemplary two-dimensional graphical representation 215 that depicts rates at which a patient's non-cardiac muscle activity signals in the patient's ECG waveform exceeded any of three different intensity levels (e.g., low, medium, and high). In various examples, any number of intensity levels and threshold criteria may be specified by the reviewing medical personnel to produce a chart with some further qualitative information about the activity.

In the depicted example, 12 total events were detected both in time interval 6 and again in time interval 10. In time interval 10, the events were primarily low intensity, and no high intensity events were detected. In time interval 6, the detected events were of several different intensity levels, including 2 high intensity events. Accordingly, a reviewing health care provider can advantageously review the breakdown of events by intensity to rapidly evaluate the patient's physical activity level during various time intervals based on both the quantity and the quality of their non-cardiac muscle activity.

FIG. 2D shows an exemplary two-dimensional graphical representation 220 that depicts rates at which non-cardiac muscle activity signals in the patient's ECG waveform exceeded any of three different durations (e.g., short, medium, and long). In various examples, any number of duration levels and threshold criteria may be specified by the reviewing medical personnel to produce a chart with some further qualitative information about the activity.

In the depicted example, 10 short duration events were detected both in time interval 7 and again in time interval 10. In time interval 10, the events were primarily short duration, and no long duration events were detected. In time interval 7, the detected events were of several different intensity levels, including 9 long duration events. Accordingly, a reviewing health care provider can advantageously review the breakdown of events by duration to rapidly evaluate the patient's physical activity level based on both the quantity and the quality of their non-cardiac muscle activity over a number of time intervals.

FIG. 2E shows an exemplary three-dimensional graphical representation 225 that is similar to FIGS. 2A-2B in that it depicts in one dimension (labeled "Events") the number of times that non-cardiac muscle activity signals in the patient's ECG waveform were detected. In an orthogonal dimension (labeled "Integral"), the graphical representation 225 further indicates a time integral (e.g., numerical integration, analog integration, or accumulation over time) of the intensity of patient's non-cardiac muscle activity signal that was accumulated throughout each time interval. In various examples, any number of integrator gain (e.g., scale factor) values may be specified by the reviewing medical personnel to produce a chart with some further qualitative information about the activity of the patient.

In the depicted example, a similar number of events were detected both in a time interval 230 and again in a time interval 235. However, the integral value in the time interval 230 is substantially higher than the integral value in the time interval 235. This indicates that for the same number of events, the patient's activities were significantly more intense and/or of longer duration during the time interval 230. Accordingly, a reviewing health care provider can advantageously review the breakdown of events as an integration of intensity levels of non-cardiac muscle activity during each of a number of time intervals to rapidly evaluate the patient's physical activity level based on both the quantity and the quality of their non-cardiac muscle activity.

The portion of the ECG waveform acquired during each of a number of user-specified time intervals may be processed to identify non-cardiac muscle activity information. The identified muscle activity information is then accumulated to determine an activity level to display in the specified time interval of the graphical representation 105.

In various examples, the time intervals used for display of the patient activity information may be specified to span certain sequential periods of time (e.g., every 5 minutes, every 15 minutes, every hour, every 3 hours, every 12 hours, every 24 hours, every week, every month, or any other suitable time interval). In other examples, non-sequential (e.g., separated by gaps of time) and/or non-uniform (e.g., different spans of time) time intervals may be specified for processing or display. For example, exemplary non-uniform time intervals may include a time interval specified to span sleeping hours, followed by a time interval over the morning wake time for the patient, followed by an afternoon time interval and an evening time interval.

Figure 3A:
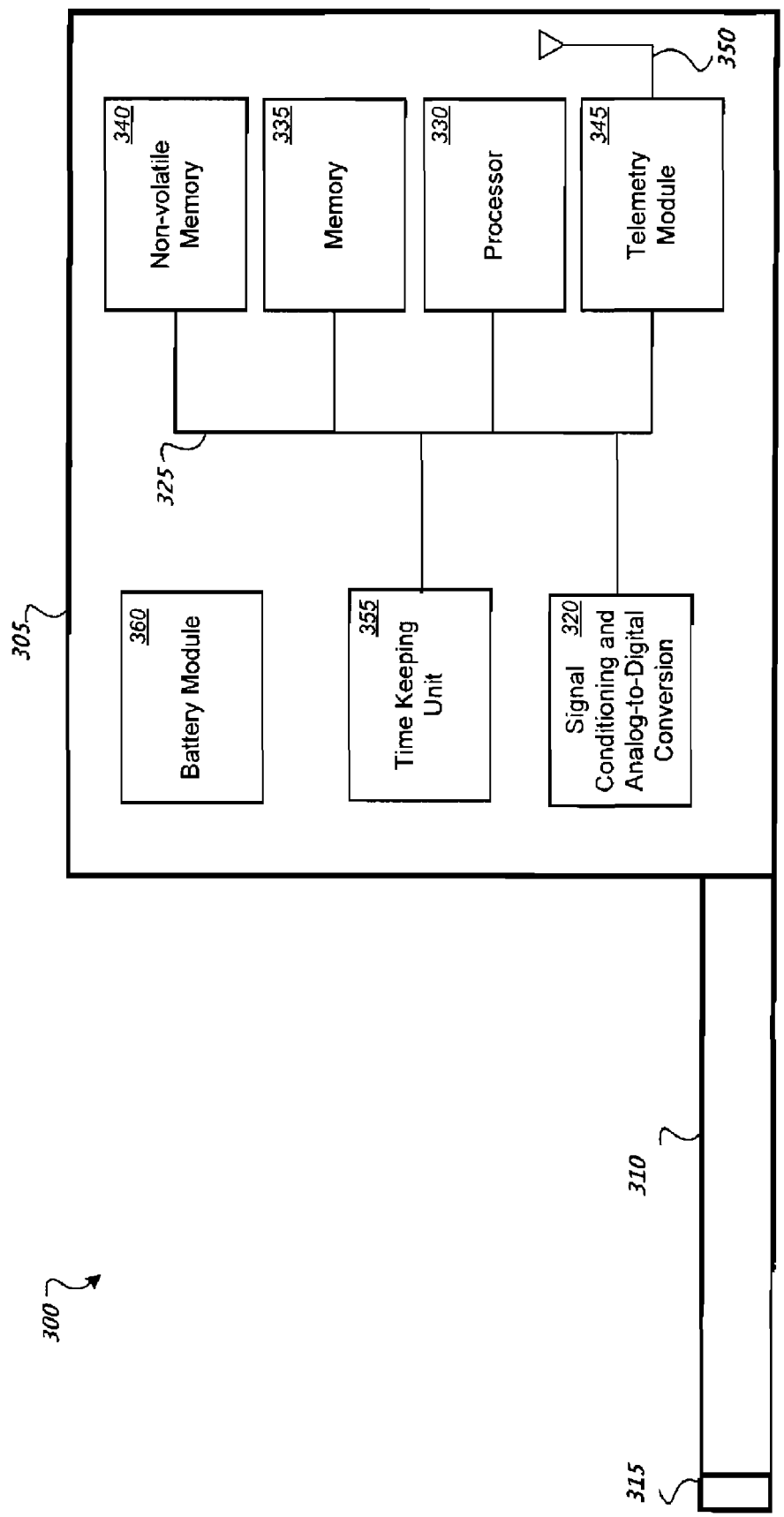
FIG. 3A shows an exemplary medical device configured for subcutaneous cardiac rhythm monitoring that includes receiving ECG waveforms.

FIG. 3A shows an exemplary medical device 300 configured for monitoring subcutaneous cardiac rhythms by receiving ECG waveforms. In an illustrative example, the medical device 300 may be used as the medical device 110 described with reference to FIG. 1A. The device 300 includes a housing 305, a lead 310, and an electrode 315 adapted to be positioned in or around a heart, or over a skeletal muscle such as the chest muscle. In some other examples, the medical device may have one or more additional leads with one or more additional electrodes for detecting ECG waveforms.

In some embodiments, at least a portion of the housing 305 may be conductive to serve as an electrode for sensing ECG waveforms. In some embodiments, at least a portion of the housing 305 may be positioned in close proximity or in at least partial direct contact with non-cardiac tissues that generate and/or conduct electrical signals associated with non-cardiac muscle activity. For example, one exemplary method involves positioning the housing 305 in substantially direct contact with muscle fascia. Sensitivity to electrical signals associated with non-cardiac muscle may advantageously be improved by positioning the housing 305 or another subcutaneous electrode in close proximity to muscle fascia in a pectoral region, for example. Further improvements to sensitivity to non-cardiac muscle activity signals superimposed on an ECG waveform may be realized by substantially reducing or eliminating an insulative coating from portions of the housing 305 that serve as an ECG electrode. In some embodiments, an insulative coating, such as parylene, is removed, substantially reduced in thickness, or not applied to at least a portion of the exterior of the housing 305.

Signals received by the electrode 305, 315 are communicated to a signal conditioning and analog-to-digital conversion module 320 in the housing 305. The module 320 includes analog signal conditioning circuitry to, for example, limit, filter, amplify, attenuate, rectify, and/or sample the received ECG waveform as a continuous-time analog signal. In some examples, the analog signal conditioning in the module 320 may divide the ECG waveform at some point for processing in two substantially separate signal processing chains: one for ECG monitoring of electrical signals associated with cardiac activity, and one for detecting electrical activity associated with non-cardiac activity. For example, to the extent that ECG signals have lower frequency components than non-cardiac muscle signals exhibit, a signal processing chain to detect non-cardiac muscle activity may provide substantially more attenuation (or less amplification) of low frequencies than the ECG signal processing chain provides. For instance, ECG signals may include frequency contents with substantial energy between about 10 Hz and about 20 Hz, with some components at higher frequencies, but in general under about 150 Hz. One reference, Medical instrumentation, John G Webster Editor, Chapter 6, page 259, published by John Wiley and Sons, 1998, $3^{rd}$ edition ISBN 0-471-15368-0, describes example EMG signals as including frequency components between about 25 Hz and about 2 kiloHertz.

In some implementations, analog signal conditioning of the non-cardiac muscles signals may be supplemented and/or substantially replaced by digital signal processing that is performed on samples (e.g., a digital representation) of the ECG waveform. For example, digital signal processing techniques may supplement and/or substantially replace analog signal conditioning circuitry to discriminate and separately process (e.g., filter, amplify, detect, and/or characterize) non-cardiac muscle noise information from ECG information.

After sampling and conversion to a digital representation in an analog-to-digital conversion process, the ECG waveform may be stored in a memory location and/or processed (e.g., in a digital FIR filter). In the depicted example, the samples are communicated over a digital bus 325 for processing by a processor 330, storage in a memory 335 or a non-volatile memory (NVM) 340, and/or a transmission by a telemetry module 345 via an antenna 350. Handling of the sampled data may be supervised by the processor 330, which may be supplemented by one or more processing elements configured to supervise, control, and monitor operations by executing instructions retrieved from storage in a memory, such as the NVM 340.

The depicted embodiment further includes a time keeping unit (TKU) 355, which may associate time stamp information (e.g., date and time to within fractions of a second) with sampled data, and a battery module 360 to supply power to operate the device 305. In some examples, the TKU 335 includes a real time clock, and/or a substantially stable time reference (e.g., oscillator) to which time intervals may be synchronized. Some embodiments use the time stamp information to determine which segments of the ECG waveform to process when determining non-cardiac muscle activity during a specified time interval. In other examples, time information from the TKU 355 may be associated with processed information (e.g., intensity, duration, integral contribution) about each non-cardiac muscle activity event so that the event and time information may be communicated as a packet of information via the telemetry module 345.

For example, the processor 330 may supervise various operations, such as waveform data collection and transdermal communications. The processor 330 may include one or more of the following: a math coprocessor, an ASIC (application specific integrated circuit), DSP (digital signal processor), discrete or integrated analog and/or digital circuits, and a dedicated digital logic architecture to perform mathematics functions, for example. The math coprocessor may perform various operations that include floating point arithmetic, signal processing, digital filtering (e.g., IIR, FIR) and/or numerical operations (e.g., curve fitting, numerical derivative computation, numerical integration, fast Fourier transformation (FFT), and interpolation).

In some embodiments, the processor 330 may also perform operations in response to input data or commands received via a wireless (e.g., transdermal) communication link. For example, programming instructions and or commands may be executed as received via the antenna 350.

In this example, the NVM 340 is coupled to the processor 330 by the digital address/data bus 325. The processor 330 may execute instructions and retrieve information stored in the NVM 340 via the bus 325. The NVM 340 may include a number of code modules (not shown) containing instructions that, when executed by the processor 330, cause the performance of, for example, ECG waveform measurement operations, or house-keeping operations in support of the device 300 (e.g., user interface, programming, boot-up, configurations, and the like).

In some embodiments, an analog version of the ECG signal may be coupled to a control input of the telemetry module, which is configured to modulate a continuous (e.g., analog) transmission carrier signal (e.g., AM (amplitude modulated), FM (frequency modulated), PM (phase modulated), frequency shift keying (FSK), pulse-width modulated (PWM), etc . . . ) to communicate raw or partially processed ECG waveform information in an analog domain to a receiver outside the patient, such as the local communication module 130, which may retransmit or further process the ECG waveform in the analog and/or digital domains.

In some examples, some processing operations to detect non-cardiac muscle activity events may be implemented with hardware components and/or digital signal processing, that apply, for example, frequency selective filtering (e.g., highpass, low-pass, band-pass, band-reject) to the received waveform. Further exemplary processing of the received waveform in an analog domain includes a rectification stage, followed by a filtering (e.g., capacitive) stage, and a threshold detection module to detect when the filtered signal satisfies one or more fixed or user-specified (e.g., variable) threshold criteria.

Figure 3B:
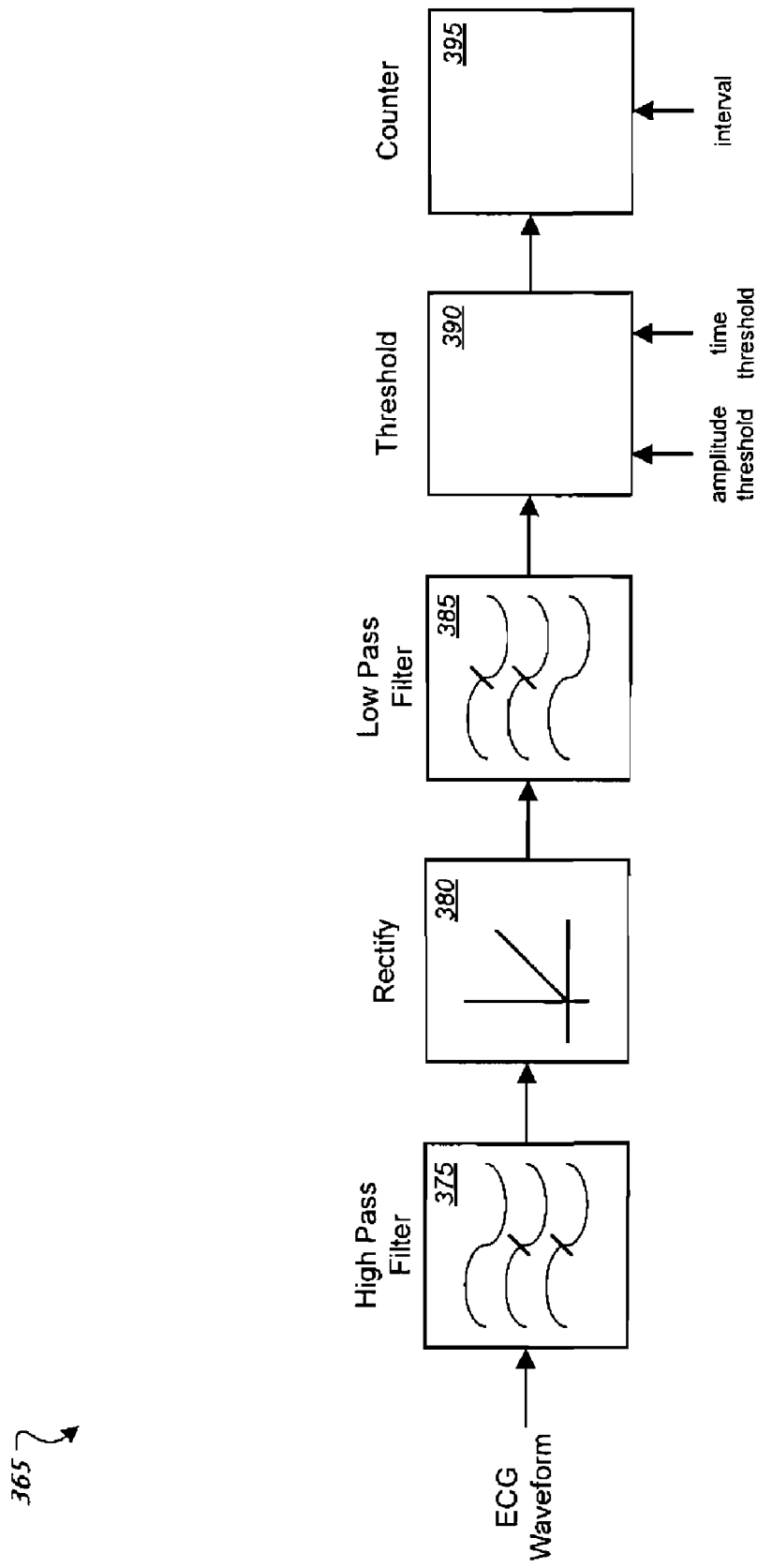
FIG. 3B shows an exemplary signal processing chain to detect and measure non-cardiac muscle activity episodes in an ECG waveform.

FIG. 3B shows an exemplary signal processing chain 365 to detect and measure non-cardiac muscle activity episodes in an ECG waveform. In various implementations, this may be implemented in part or entirely in either the analog domain or the digital domain. With reference to FIG. 1A, any of the aspects of the signal processing chain 365 may be implemented in any node of the system 100, including but not limited to the medical device 110, the local communication module 130, the remote data processing facility 135, the remote access node 140, or the clinic 145.

In this example, the signal processing chain 365 includes a high pass filter module 375, a rectification module 380, a low pass filter module 385, a threshold module 390, and a counter module 395.

The high pass filter module 375 may attenuate low frequencies, such as the low frequencies evident in the typical ECG waveform 195 of FIG. 1B. Accordingly, the module 375 substantially removes at least some low frequency components of the electrical signals that are associated with the heart, but without substantially attenuating signal components in the frequency range of interest, including signal components associated with non-cardiac muscle activity. In an analog example, a high pass filter may include a series capacitance, as is well known in the art.

The rectification module 380 and the low pass filter module 385 may be considered to operate like an envelope detector that substantially tracks an envelope of the peaks of oscillations, with some decay over time. This also converts the high frequency signal components associated with non-cardiac muscle activity into a unidirectional voltage signal that is suitable for comparison to a threshold.

The threshold module 390 compares the output of the module 385 to one or more thresholds. Each threshold that is used for detecting non-cardiac muscle activity events is independently adjustable via an amplitude threshold input and a time threshold input. To detect a non-cardiac muscle activity event, for example, the input to the module 390 must be over a specified amplitude threshold for at least a specified time threshold. This may reduce responding to short duration noise glitches (e.g., electromagnetic interference, electrostatic discharge, or the like). Some embodiments may employ a user-specifiable amount of hysteresis, whereby a second (e.g., lower) amplitude threshold may be specified such that in order to detect an event, the input signal must exceed the first (higher) threshold and then remain above the second (lower) threshold for at least the specified time threshold. In various embodiments, multiple compound time-threshold functions may be specified (e.g., with or without hysteresis) as criteria for detecting various levels of non-cardiac muscle activity events.

Upon detecting a non-cardiac muscle activity event, a signal is sent to increment a counter in the counter module 395. The counter module 395 of this example is reset by a signal on an interval input, which is activated at the start or end of every time interval. Upon detecting the start of a time interval, the counter is reset to zero. Upon detecting the end of a time interval, the count is stored in a memory for subsequent processing or display in a graphical representation, such as the graphical representation 105 of FIG. 1A.

In other embodiments, the threshold module 390 may further measure and/or record amplitude as a measure of intensity, and the intensity value may be displayed in a graphical representation such as the example described with reference to FIG. 2C. Similarly, the threshold module 390 may further measure and/or record time over a threshold (or compound threshold) as a measure of duration, and the duration value may be displayed in a graphical representation such as the example described with reference to FIG. 2D.

In some embodiments, the threshold module 390 may measure and/or record a time integral of the intensity throughout a time interval, and the integral value may be displayed in a graphical representation such as the example described with reference to FIG. 2E. For example, the integration may accumulate intensity in excess of a threshold. In the analog domain, integration circuits may be used, and their outputs may optionally be sampled, and reset so that integration only occurs while a non-cardiac muscle activity event is active. As such, the integral result for a time interval may be a sum of the integrated values that were sampled and recorded during the time interval. Similarly, numerical integration may be performed in the digital domain whenever a non-cardiac muscle activity event is active.

In other embodiments, the signal processing chain may further include amplification (e.g., differential) or frequency shifting (e.g., by mixing with a higher frequency for filtering purposes).

Figure 4A:
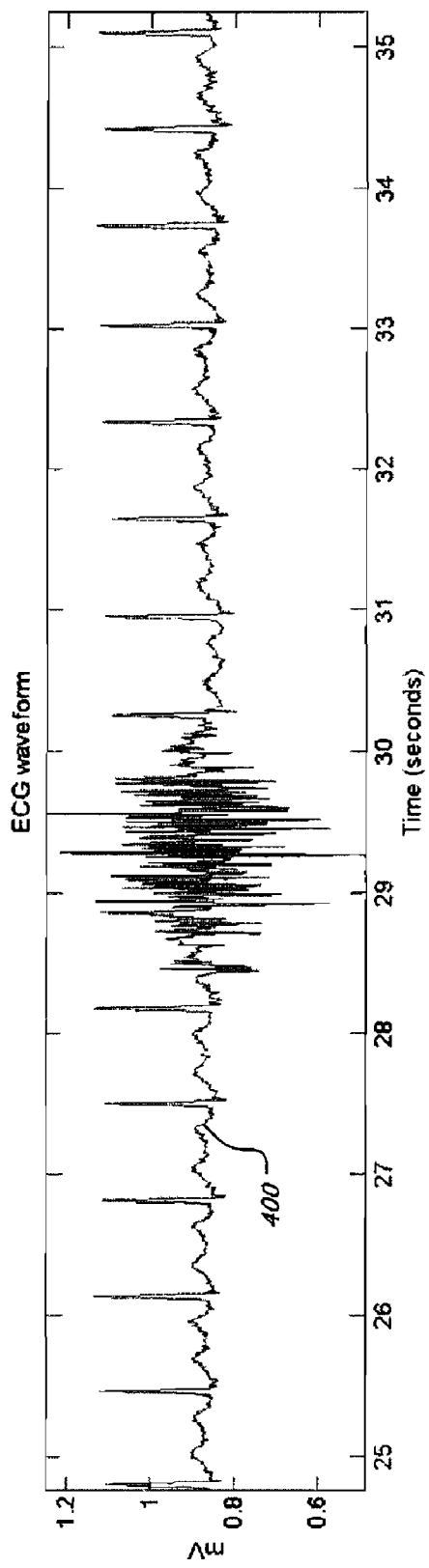
FIG. 4A shows a typical ECG waveform plotted on a chart in which the x-axis represents the time in seconds and the y-axis represents the voltage in millivolts.
Figure 4B:
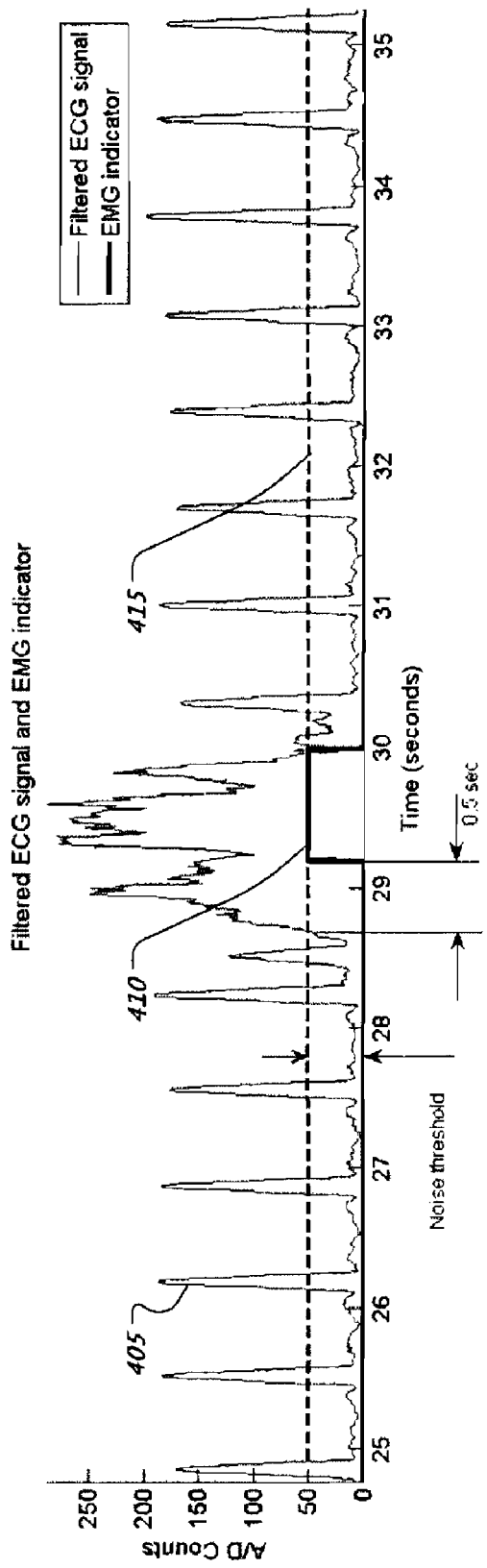
FIG. 4B shows an example of a processed ECG waveform, which represents a version of the ECG waveform of FIG. 4A after processing to identify non-cardiac muscle activity events.

FIG. 4A shows a typical ECG waveform 400 plotted on a chart in which the x-axis represents the time in seconds and the y-axis represents the voltage in millivolts. FIG. 4B shows an example of a processed ECG waveform 405, which represents a version of the ECG waveform 400 after processing to identify non-cardiac muscle activity events. In some examples, the processed ECG waveform 405 may use a channel of an ECG monitor that is normally used for R-wave detection. The waveform 405 is a high-pass filtered, rectified, and smoothed version of the original ECG waveform 400. Non-cardiac muscle activity events are indicated by a rectangular area 410. In this example, the criteria for detecting non-cardiac muscle activity events are that the minimum rectified signal amplitude is above a user-specified threshold voltage 415 (e.g., 50 A/D counts) for a user-specified duration (e.g., 0.5 seconds). The rectangular area 410 at the bottom of the graph indicates when the foregoing exemplary criteria are met in this example.

Figure 5:
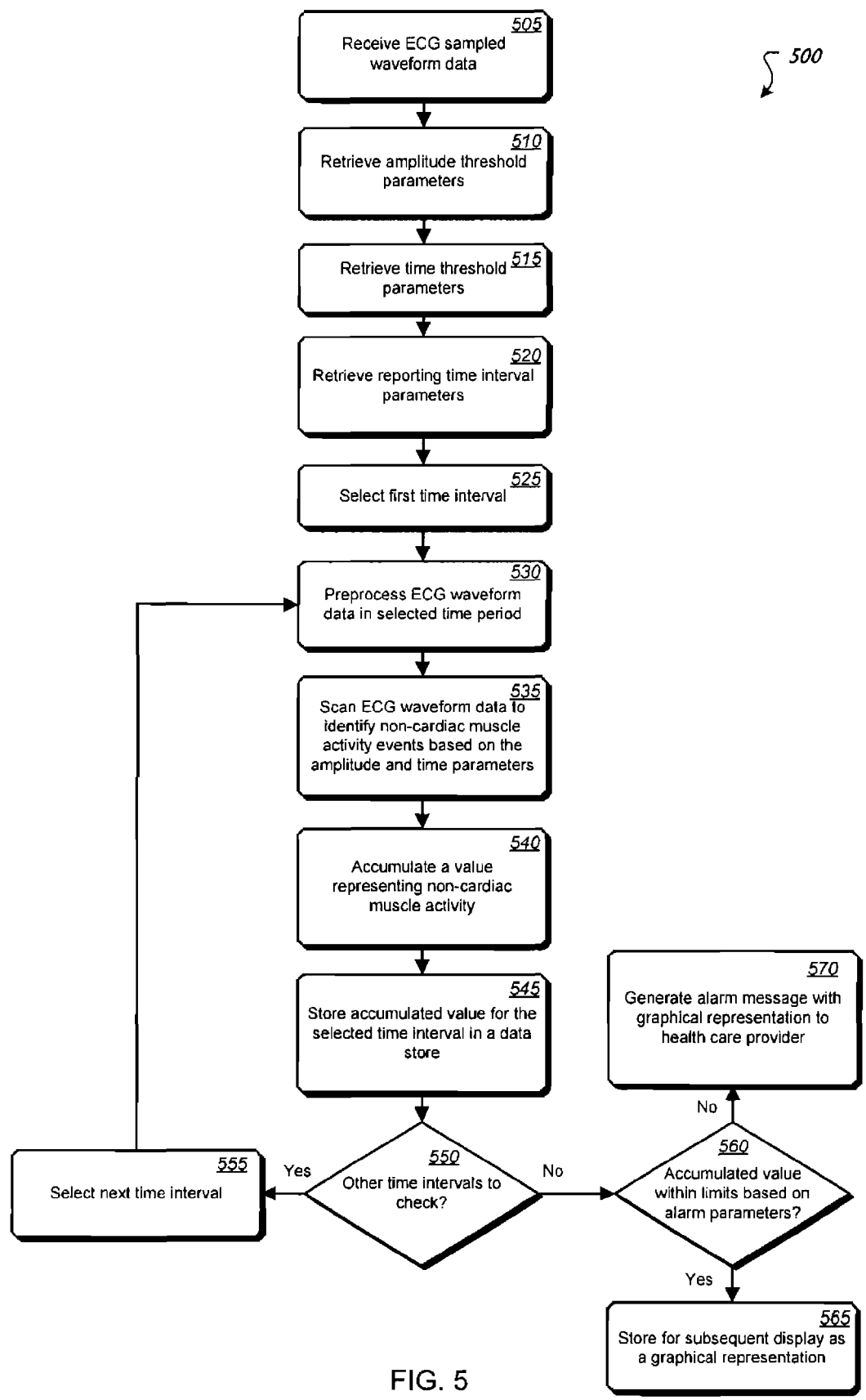
FIG. 5 shows an exemplary diagnostic method for processing ECG waveforms to detect non-cardiac muscle activity, and to notify a patient's health care provider if the detected activity indicates that the patient's activity level is out of a healthy range.
Figure 6:
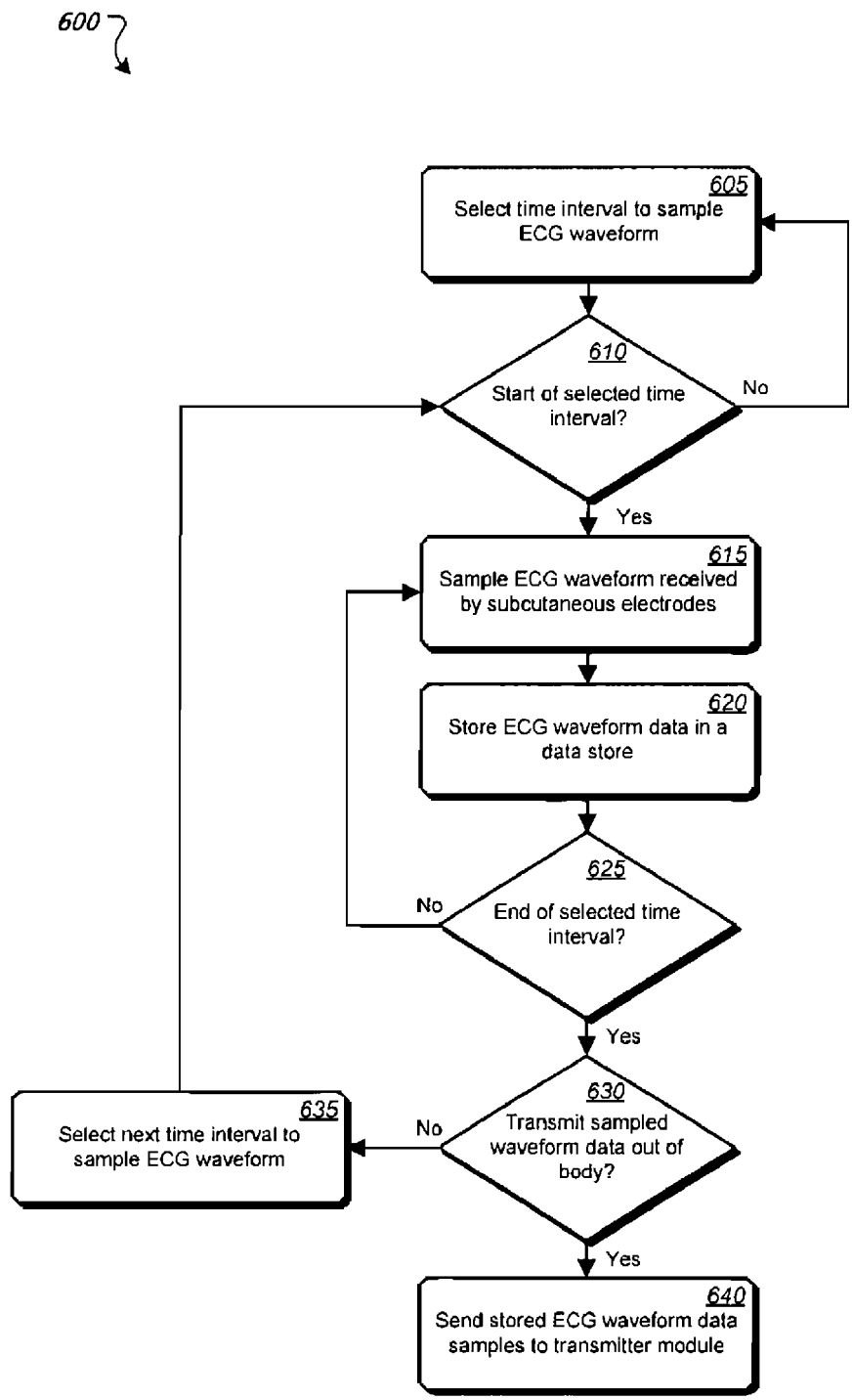
FIG. 6 shows an exemplary diagnostic method for operating a device implanted with subcutaneous electrodes to collect ECG waveforms, and to transmit the ECG waveforms out of the patient for post-processing.

FIGS. 5-6 illustrate some exemplary processes associated with various components of the system 100 of FIG. 1A. Some or all of the steps of these processes may be performed by one or more processors executing instructions, which instructions may be encoded in one or more code modules stored in at least one data store.

FIG. 5 shows an exemplary diagnostic method 500 for processing ECG waveforms to detect non-cardiac muscle activity, and to notify a patient's health care provider if the detected activity indicates that the patient's activity level is out of a healthy range. In some examples, the notification may include a graphical representation of the patient's activity level in each of a number of time intervals, as shown for example in the graphical representations 105 of FIG. 1A, or those described with reference to FIGS. 2A-2E. In the illustrative example described with reference to FIG. 1A, some or all of the steps of the method 500 may be performed in any or each of the remote data processing facility 135, the remote access node 140, and/or the clinic 145.

The method 500 includes receiving ECG sampled waveform data at step 505. This may occur via a communication link from the local communication module 130, or from a database in the facility 135 that contains previously stored ECG waveform data samples collected by an implanted medical device, such as the medical device 110. At steps 510-520, a processor, such as the processor 155, retrieves amplitude threshold parameters, time threshold parameters, and time interval parameters, such as those described with reference to the threshold module 390 and the counter module 395 of FIG. 3B. The parameters of steps 510-520 may be adjusted or specified by health care providers, programmed as a fixed value within an implanted ECG monitor device, adjusted according to a measured baseline for the patient, and/or set according to statistical norms for the patient's peers (e.g., similar age, weight, health status, sex, or the like). For example, the time interval parameters may specify uniform-length, adjacent-in-time intervals (e.g., hourly, every 90 minutes, and so on), or custom time intervals, which may be non-uniform and have intervals separated by gaps in time.

Having retrieved the parameters for processing the ECG waveform data, a first time interval is selected at step 525 to process the ECG waveform samples. At step 530, samples of the ECG waveform within the selected time interval are preprocessed to produce a waveform representative of electrical signals associated with non-cardiac muscle activity, for example, as described with reference to modules 375-385 in FIG. 3B, with reference to waveform 405 in FIG. 4B, and elsewhere herein. The retrieved time and amplitude threshold parameters are then applied in step 535 to scan the preprocessed waveform to identify non-cardiac muscle activity events. Examples of step 535 are described with reference to the threshold module 390 in FIG. 3B or to the areas 410 in FIG. 4B. After identifying the events, one or more values representing non-cardiac muscle activity are accumulated, at step 540, for the selected time period. Accumulated values may include, but are not limited to, a number of events, average event intensity, average event duration, weighted sum of events as a function of intensity and duration, and a time integral of the intensity. The accumulated information for the selected time interval is stored in a data store at step 545 for subsequent retrieval and rendering, for example, as a portion of a histogram of patient activity level in the selected time interval.

If, at step 550, other time intervals have been requested to be checked for non-cardiac muscle activity, then another time interval is selected at step 555, and the step 530 is repeated. Otherwise, a processor checks at step 560 whether all of the accumulated values are within predetermined limits according to specified alarm parameters. Predetermined limits and alarm parameters may be stored, for example, in the rules database 160 of FIG. 1. In some examples, predetermined limits reflect a range of healthy levels of physical activity for the patient, or trends in the patient's physical activity levels (e.g., the rate of change in the patient's physical activity may be increasing or decreasing too rapidly). If the accumulated values are within limits, then the accumulated value information for each of the time intervals selected for the method 500 is, at step 565, stored in a data store for subsequent retrieval and display as a graphical representation. Otherwise, at step 570, an alarm message is generated to notify the health care provider team, and optionally contact the patient, about the potentially unhealthy level of physical activity. In one embodiment, the alarm message is an electronic mail message that contains an attached graphical representation of the patient's activity level over the relevant time intervals of interest.

In one embodiment, the alarm parameters of step 560 may include criteria for comparing qualitative information about the patient's physical activity levels to prescribed normal ranges. For example, if 10 levels of duration or intensity are monitored, then an alarm condition may be set for each of the levels. In one example, an alarm condition occurs if more than 3 events at an intensity level of 9 out of a maximum of 10 are detected within a particular time interval. The alarm condition profile may have different minimum and/or maximum limits, and the limits may be adjusted according to time of day. For example, a low priority alarm may be activated if the patient repeatedly has more than an average of 3 medium intensity events very early in the morning during normal sleeping hours. This may indicate that the patient is not getting sufficiently restful sleep, for example. Similarly, if a patient is averaging less than a minimum number of medium duration physical activity events during the day, a physician may want to call the patient and inquire about his declining activity and related symptoms, or counsel the patient to increase exercise activities.

FIG. 6 shows an exemplary diagnostic method 600 for operating a device implanted with subcutaneous electrodes to collect ECG waveforms, and to transmit the ECG waveforms out of the patient for post-processing, for example, according to the method 500 of FIG. 5. In the illustrative example described with reference to FIG. 1A, the steps of the method 600 may be performed by the medical device 110.

The method 600 includes selecting a time interval to sample an ECG waveform at step 605. In some embodiments, the ECG waveform may be sampled substantially continuously, periodically, or at specified time intervals. In one example, a processor cooperates with a time keeping unit, such as the TKU 335 described with reference to FIG. 3A, to determine if the current time is within the selected time interval. At step 610, step 605 is repeated until the start of the selected time interval. Upon the start of the selected time interval, sampling is performed to convert an analog ECG waveform received by subcutaneous electrodes to a digital representation at step 615. At step 620, the sampled ECG waveform data point is stored in a data store. At step 625, step 615 is repeated until the end of the selected time interval is reached. After reaching the end of the selected time interval, a check is made at step 630 whether or not to transmit the sampled waveform out of the body.

In this example, if the processor is not instructed to transmit the sampled waveform data out of the body, then the processor selects a next time interval to sample the ECG waveform at step 635, and the step 610 is repeated. Otherwise, the processor sends the stored data to a transmitter module. In the example of FIG. 3A, sampled ECG waveform data stored in the memory 335 may be transferred to the telemetry module 345 for transmission to the local communication module 130 outside of the body.

In an illustrative example, an instruction whether or not to transmit the sampled ECG waveform out of the body (at step 630) is stored as a flag in a register that is programmed using, for example, the local communication module 130 or a handheld programming device that communicates with the implanted medical device 110. A request to transmit sampled ECG waveform data may originate from any node in the system 100, including but not limited to any of the remote data processing facility 135, the remote access node 140, and/or the clinic 145.

In another embodiment, the sampled ECG data may be queued for transmission (step 620) as the sampled data is stored in a memory device. In some implementations, a packet of information may include a data payload representing a number of sequential data samples obtained by repeating step 615. In one example, the payload contains only a portion of the samples for the entire time interval. A data stream containing one or more communication packets with sampled data information may further include other parameters, which may include, but are not limited to, patient or device identification information, time stamp information, sampling rate, gain and/or phase settings for the analog-to-digital conversion, or other configuration settings of the medical device 110, as well as encryption, error detection (e.g., checksum), and/or error correction (e.g., error correction code) information.

In various examples, the samples stored in a memory of the implanted medical device 110 may be partially processed (e.g., using FIR, decimation, or other digital signal processing techniques) prior to transmission out of the body.

Figure 7:
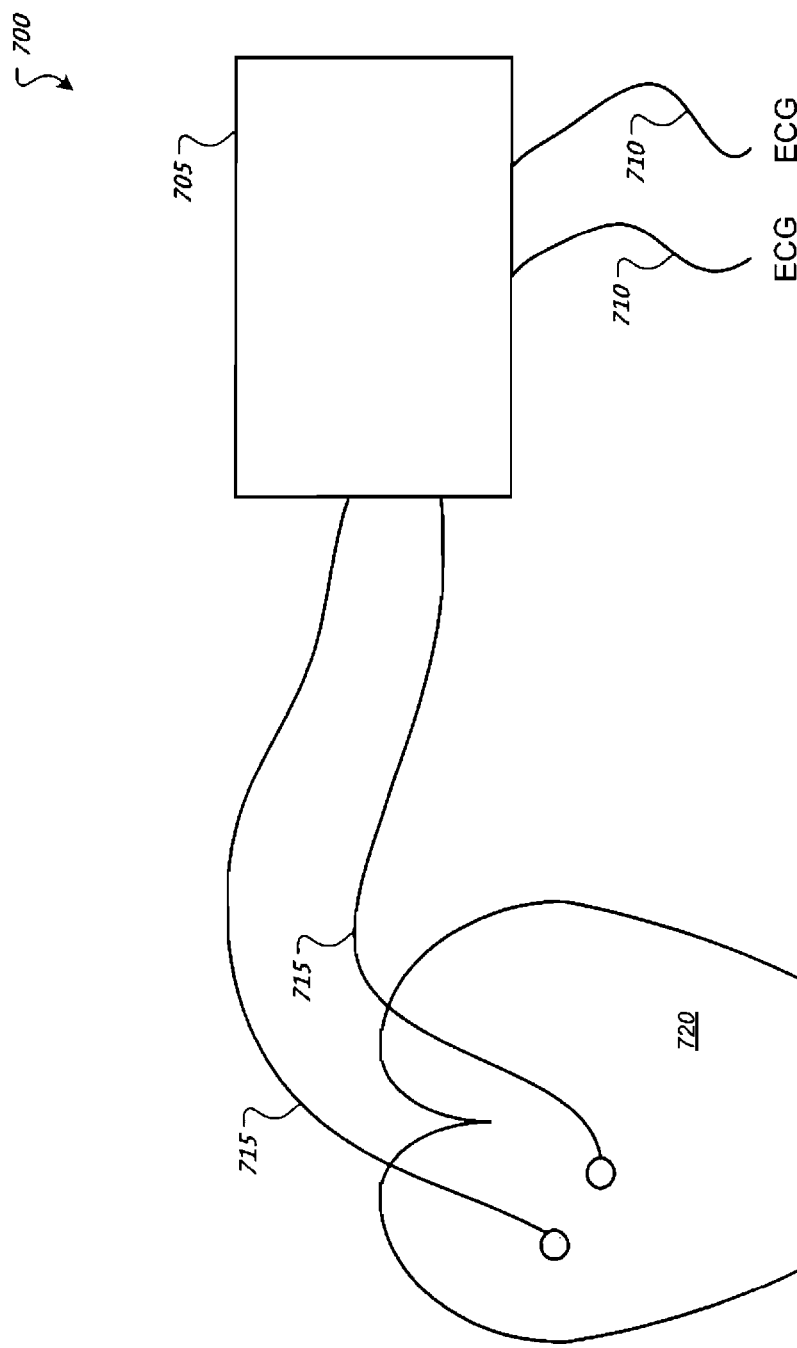
FIG. 7 shows an exemplary therapeutic system configured to dynamically control cardiac stimulation based on physical activity information derived from an ECG waveform.

Various examples of diagnostic apparatus and methods have been described with reference to FIG. 1A-FIG. 6. FIG. 7 shows an exemplary therapeutic system 700 configured to dynamically control cardiac stimulation based on physical activity information derived from an ECG waveform.

The therapeutic system 700 includes a medical device 705 that is implantable within a body of a patient and configured to provide pacing responsive to an indication of physical activity level derived from ECG waveform information. The medical device includes a set of leads 710 with subcutaneous electrodes for sensing ECG waveforms, and a set of leads 715 for applying electrical stimulation to a heart 720 in the patient. The device 705 is, for example, a pacemaker that applies an electrical stimulus through the leads 715 to stimulate the heart 720 to beat at a prescribed pacing rate. In various examples, the system 700 provides a form of cardiac resynchronization therapy (CRT), and/or provides subcutaneous electrical stimulation for therapeutic pacing, cardioversion, and/or defibrillation. In some other embodiments, the leads 715 may be omitted, for example, if one of the leads 715 includes an intra-cardiac electrode or epicardial electrode, in combination with a can electrode on the housing on 705, that provides both for muscle noise detection by sensing of the heart signals and for therapeutic stimulation.

The electrical stimulation applied to the heart 120 is dynamically controlled based on physical activity levels determined by processing one or more ECG waveforms received by the device 705. Exemplary processes and apparatus for processing ECG waveforms to identify and characterize non-cardiac muscle activity events are described elsewhere herein, such as with reference to FIG. 5, for example.

In particular, the device 705 can operate in a mode that is responsive to non-cardiac muscle activity signals detected on the ECG waveform signals. For example, as the number, intensity, duration of non-cardiac events increases, a corresponding change may be applied to the pacing rate. For example, pacing rate may be increased upon sensing increased activity level. Some embodiments may be responsive to a moving average of physical activity. Various operating parameters (e.g., time delay, acceleration, minimum rate, maximum rate, and ratio of pacing rate to activity level may be programmable, either locally or remotely, by a physician, and/or programmed to a predetermined (e.g., default) level. In some implementations, a pacing rate offset may be used for exercise conditions. Some implementation may include a time delay for changing a pacing rate in response to changes in the intensity, duration, and/or number of activity events detected. For example, pacing rate profile may be substantially maintained for a predetermined time period (e.g., about 5, 10, 15, 20, 25, 30, 35, 40, 45, 50, or about 60 seconds or more) after detecting a change in activity level. The time delay may be a function of current activity level, whereby the response delay may be longer at low activity levels and shorter at higher activity levels. In some examples, one or more acceleration and/or deceleration rates may be programmed as a function of recent activity levels as determined from non-cardiac muscle activity derived from ECG signals, such as for periods during or after exercise. Examples of techniques (e.g., rate adaptive pacing) for controlling pacing rate based on activity are described in U.S. Pat. Nos. 5,243,979, 6,449,508, 5,423,870, or "Rate Adaptive Pacing", edited by David G. Benditt, Boston: Blackwell Scientific Publications, copyright 1993.

In accordance with various techniques that have been described herein, the device 705 acquires ECG waveform by monitoring electrical signal potentials detected by the set of leads 710. In this example, ECG waveform signals may be monitored among any of the leads 710, 715. In some examples, at least one of the subcutaneous leads is an exposed conductive surface portion of a housing of the device 705. In some embodiments, an insulative coating (e.g., parylene) is partially or substantially removed or eliminated from at least a portion of an external conductive surface of the device 705, which may advantageously increase sensitivity to non-cardiac muscle electrical signals. The housing of the device 705, and/or one or more subcutaneous ECG electrodes, may be positioned substantially proximate non-cardiac muscle tissues so as to increase coupling to electrical signals associated with non-cardiac muscle activity.

Figure 8:
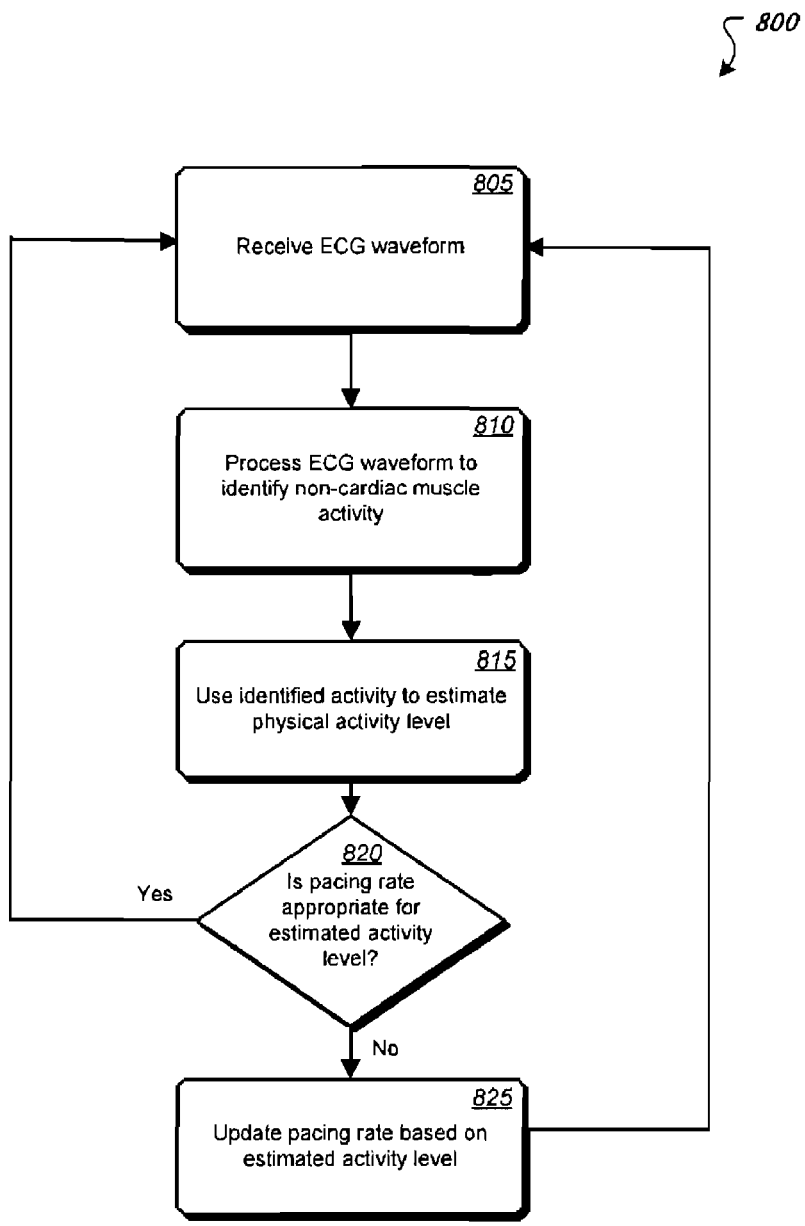
FIG. 8 shows an exemplary therapeutic method for updating a pacing rate in response to estimated physical activity levels derived from ECG waveforms.

FIG. 8 shows an exemplary therapeutic method 800 for updating a pacing rate in response to estimated physical activity levels derived from ECG waveforms. In an illustrative example, the method 800 is performed by the medical device 705 of FIG. 7.

The method 800 includes a step 805 in which an ECG waveform is received. ECG waveforms are received, for example, by a processor (not shown) in the device 705. The received ECG waveform is processed at step 810 to identify non-cardiac muscle activity. Examples of identifying non-cardiac muscle activity have been described above, including measurements of frequency, intensity, and or duration of non-cardiac muscle activity events. In some examples, the processing may further include a weighted moving average that attenuates the contributions (e.g., weights) of samples based on proximity in time to the present time. In some examples, the processing may be performed within the device 705.

At step 815, the identified non-cardiac muscle activity event information is used to estimate a current level of physical activity. The estimated level of physical activity is, in some examples, a function of the rate, intensity and/or duration of recent non-cardiac muscle activity events.

At step 820, a determination is made whether the current pacing rate is appropriate based on the estimated activity level. In one example, this determination is made with reference to a look-up table that relates activity level to pacing rate. In some embodiments, the pacing rate may be computed as a function of activity level and one or more other parameters.

If it is determined that the pacing rate is appropriate for the estimated physical activity level, then the step 805 is repeated. Otherwise, at step 825, the pacing rate is updated based on the estimated activity level, and then the step 805 is repeated.

In some examples, acceleration/deceleration limits may be placed on the adjustment to the pacing rate in the step 825. Various gain factors (e.g., to the proportional, integral, derivative gains) may be applied in the pacing rate control system that includes the closed loop formed by feeding back the estimated physical activity level. In some embodiments, one or more control gains may be configured so that adjustments to the pacing rate exhibit a well-behaved (e.g., slightly over-damped, slightly under-damped, stable) response. For example, the pacing rate control system may be tuned so that the pacing rate exhibits substantially low overshoot, but without excessively sluggish response times that would cause the pacing rate to substantially lag a desired response to the current physical activity level.

In some embodiments, the ECG information received by the device 705 may be transmitted out of the patient's body for post-processing. In some examples, sampled ECG waveform data is transmitted to a local communication module located outside of the patient. The ECG waveform data may be communicated to a local or to remote processor for post-processing to identify patient activity level information.

In an illustrative embodiment, ECG waveform data may be communicated among nodes of the system 100 of FIG. 1. One or more steps of the method 500 of FIG. 5 may be performed to post-process the ECG waveform data in one or more of the local communication module 130, the remote data processing facility 135, the remote access node 140, and/or the clinic 145.

After post-processing the ECG waveform to identify a level of non-cardiac muscle activity, a decision is made at one of the nodes in the system 100 about whether to increase, decrease, or maintain a current pacing rate at which the device 705 electrically stimulates the heart 720. Referring to the example of FIG. 1A, that determination may be communicated to the device 110 via the local communication module 130. In some embodiments, the activity level information is communicated to the medical device 110, and the medical device determines whether and how to adjust a pacing rate in accordance with programmed rules stored in a data store in the device 110. In various embodiments, the frequency, period, amplitude, duty cycle, waveform shape, and/or polarity of electrical stimulation to an organ in a patient may be controlled in response to a determined level of physical activity of the patient in accordance with examples described herein.

Although an exemplary system has been described, further embodiments and applications are contemplated. For example, the various diagnostic and therapeutic techniques may be applied to humans as well as other species, for example. Some embodiments may further be applied to collect and/or process ECG waveform statistical data for patient studies in clinical, pharmaceutical, and/or research applications.

Although depicted in FIG. 1A in a stand-alone (e.g., desktop) configuration, other embodiments of the local communication module 100 are implemented as a body-worn device, such as a necklace or belt-worn device carried by the patient 115. The wireless link may communicate unidirectional or bidirectional information flows between the implanted medical device 110 and the module 130. The wireless link may be implemented using a variety of techniques, such as amplitude, phase, and/frequency modulation (e.g., AM, FM, spread spectrum, or the like), and may use, for example, optical (e.g., infrared), audio (e.g., ultrasonic), and/or electromagnetic field (e.g., radio frequency) signal transmission modes.

The communication links among the remote data processing facility 135, the local communication module 130, the remote access node 140, and the clinic 145 may be wired, wireless, and/or optical (e.g., fiber-optic), or a combination thereof. At least a portion of some links may include aspects of the Internet, a VPN (virtual private network), LAN, WAN, MAN (metropolitan area network), or the like.

In various embodiments, data may be communicated unidirectionally or bidirectionally among any or all of the nodes of the system. In some embodiments, communication is unidirectional from the patient 115 to the remote data processing facility 135. In one example, data is communicated unidirectionally from the remote data processing facility 135 to the remote access node and to the clinic 145. In other embodiments, all of the data communication links among a number of nodes in the system 100 are bidirectional, such that each node can communicate commands (e.g., requests for specified parameters, time intervals, or the like), raw data (e.g., ECG waveform samples), and/or processed data (e.g., alarm notification messages, graphical representation 105) with any other node.

Some embodiments normalize the lengths of the time intervals to a reference physical activity pattern such that the graphical representation 105 will display a normalized value (e.g., 1.0) for every interval in which the measured activity levels are the same as a reference activity level during that time interval. For example, the reference activity level may represent a normal or healthy level of activity during the time interval. As an illustration, a user may select reference time intervals that include a ten hour period spanning regular sleeping hours, and a 25 minute period during a regularly scheduled exercise time, where the same activity levels are accumulated during each time interval for a desired (e.g., healthy) level of patient activity. The reference level may be customized for each patient's needs, schedule, and habits. If the measured patient activity level exceeds the reference activity levels during a time interval, then the graphical representation displays a physical activity level greater than the normalized value (e.g., above 1.0) for that time interval. Similarly, if the measured patient activity levels is below the reference activity level during a time interval, then the graphical representation displays a physical activity level below the normalized value (e.g., below 1.0) for the time interval.

In another embodiment, the graphical representation 105 is not normalized, but displays both a reference value and a measured value for each interval of time. When such a graphical representation is reviewed by a health care provider, the differences between the reference and measured physical activity levels for a number of time intervals can be determined "at a glance." In some examples, a graphical representation may represent a graph of average daily activity versus time.

In some examples, the reference value may be determined based on statistical data for typical patients with healthy activity levels. In some cases, reference values for a particular patient may be determined by monitoring physical activity levels over time to determine average or typical ranges for that specific patient. Those recorded activity levels are stored in a database. In some examples, physical activity levels are categorized as healthy or unhealthy (or graded by degree of health), by medical personnel based on a review of the stored data, either alone or in combination with one or more direct examinations (e.g., interviews, surveys) of the patient.

In an illustrative example, a reference value for each time interval may be developed by monitoring patient physical activity levels for particular time interval (e.g., 9 AM to 11:30 AM) every weekday morning. A reference value for an interval may be determined as an average or weighted average of the monitored values for that interval. In some applications, health care providers specify daily or weekly healthy profile (or range of healthy activity) for physical activity upon review of the monitored values. The specified ranges or profiles may be stored in conjunction with alarm conditions stored in a rules database.

In various embodiments, time intervals may be processed and/or displayed to distinguish between weekdays, weekends, holidays, vacations, travel periods, and other periods during which a patient's activity level may vary substantially from a typical routine. In some embodiments, the patient 115 may upload (e.g., export calendar data) for certain electronic calendar information (e.g., scheduled appointments, events, trips) to the local communication module 130 and/or the remote data processing facility 135, for example, where it is electronically stored in association with other information about the patient 115. Alarm notification criteria may be adjusted (e.g., reduced or increased sensitivity, as directed by a physician), or alarm notifications manually reviewed by an analyst or medical care provider if physical activity levels shift outside of typical ranges during periods in which non-routine activities are scheduled. Alarm notification messages may include information about the schedule calendar information, to give reviewing medical personnel access to more complete information about the status of the patient 115. In some further examples, the patient 115 may provide (e.g., by electronic message, calendar software data export, html form fill-in, or the like) schedule information about, for example, time and type of exercise or other activity information that may be displayed as annotated information associated with a corresponding time interval on the graphical representation 105. For example, a patient may indicate that they plan to walk a dog for 30 minutes every afternoon at 2:00 PM, and then watch a movie on a particular Thursdays at 7:00 PM. This information may be annotated to the corresponding time intervals displayed on the graphical representation 105, such that medical personnel have access to improved information about patient actual activities during the time intervals being reviewed. In some embodiments, the information may be displayed in a legend (e.g., text below the graphical representation 105), or in response to the reviewer operating the GUI to place a cursor over the displayed time interval of interest, or in response to user input such as a text request for information about a particular time interval. In some examples, a user may click (e.g., using a mouse, touch screen, light pen, or the like) on the histogram bar of interest to cause display of the annotated information about calendared patient activity.

In some embodiments, analog and/or digital filtering of the received waveform is performed within the medical device 110 of FIG. 1A. In some examples, a received waveform is used to modulate a carrier signal capable of transmitting an analog version of the received waveform to a receiver external to the patient 115. Accordingly, some embodiments perform analog signal processing to detect non-cardiac muscle activity events using hardware components and/or digital signal processing modules that are, at least in part, external to the patient. In some examples, analog signal processing may be partially performed within the medical device 110 and/or within the subcutaneous electrode leads, and partially performed by a processor module (not shown) in the local communication module 130 external to the patient 115. As an illustrative example, high frequency (e.g., noise) filtering and/or AC-coupling may be implemented within the medical device 110, and user-controllable tuning filters may be implemented in a local processing module external to the patient 115.

Some embodiments use digital signal processing to detect non-cardiac muscle activity events from the received ECG waveform. For example, various digital signal processing operations, which may include but are not limited to, filtering, rectification, multiplication, and the like, may be performed upon digital samples of the received ECG waveform. In various embodiments, analog to digital conversion of the received ECG waveform may be performed in the body of the patient 115 (e.g., in the medical device 110) or external to the body of the patient 115 (e.g., in the local communication module 130).

In some examples, digital signal processing to detect non-cardiac muscle activity events in the received ECG waveform is performed, at least in part, within a processor of the medical device 110. Processed or unprocessed (e.g., raw ECG waveform samples) may be transmitted via the wireless link to the local communication module 130, where further digital signal processing may be performed to detect non-cardiac muscle activity events. In one illustrative example, a processor programmed to implement a three-tap finite impulse response (FIR) low-pass filter within the medical device 110 may substantially attenuate signal content above a highest frequency range of interest for detecting muscle activity.

In one example, a processor module to detect non-cardiac muscle activity from an ECG waveform includes a low pass noise filter that is implemented in either the analog or the digital (e.g., FIR, IIR (infinite impulse response)) domain. The filter has a cut-off frequency, which may be fixed or controllable, of about 50 Hz, 100 Hz, 250 Hz, 1 kHz, 2 kHz, or at least about 5 kHz, for example.

Some systems may be implemented as a computer system that can be used with a number of embodiments. For example, various implementations may include digital and/or analog circuitry, computer hardware, firmware, software, or combinations thereof. Apparatus can be implemented in a computer program product tangibly embodied in an information carrier, e.g., in a machine-readable storage device or in a propagated signal, for execution by a programmable processor; and methods can be performed by a programmable processor executing a program of instructions to perform functions by operating on input data and generating an output. Some embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, which may include a single processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits).

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. Some examples may be implemented in a computer system that includes a graphical user interface and/or an Internet browser. To provide for interaction with a user, some implementations may be implemented on a computer having a display device, such as a CRT (cathode ray tube) or LCD (liquid crystal display) monitor for displaying information to the user, a keyboard, and a pointing device, such as a mouse or a trackball by which the user can provide input to the computer.

In various implementations, the system 100 may communicate using suitable communication methods, equipment, and techniques. For example, the system 100 may communicate with compatible devices (e.g., devices capable of transferring data within, to and/or from the system 100) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g, Wi-Fi, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

A number of implementations have been described. Nevertheless, it will be understood that various modifications may be made. For example, advantageous results may be achieved if the steps of the disclosed techniques were performed in a different sequence, if components in the disclosed systems were combined in a different manner, or if the components were replaced or supplemented by other components. The functions and processes (including algorithms) may be performed in hardware, software, or a combination thereof, and some implementations may be performed on modules or hardware not identical to those described. Accordingly, other implementations are within the scope of the following claims.

What is claimed is:

1. A method of presenting physical activity information for an individual by detecting non-cardiac muscle noise in electrocardiogram (ECG) waveform information collected by an implanted medical device, the method comprising the steps of:
    a) implanting a medical device within a patient, the medical device comprising at least a first subcutaneous electrode implanted in or adjacent to the patient's heart and a second subcutaneous electrode implanted in or adjacent to non-cardiac muscle or fascia tissue of the chest, abdomen, back or neck regions of the patient;
    b) acquiring a composite electrical waveform from the first and second subcutaneous electrodes, the composite electrical waveform comprising cardiac derived electrical signals generated by cardiac activity of the heart and non-cardiac derived electrical signals including both psychological and physiological data generated by non-cardiac muscle or fascia tissue of the patient during each of a plurality of non-overlapping time periods;
    c) post-processing at least two of the acquired composite electrical waveforms by performing the following operations:
        i) selecting one of the plurality of non-overlapping time periods;
        ii) identifying non-cardiac muscle activity events in the acquired composite electrical waveform that occurred during the selected time period;
        iii) aggregating the non-cardiac muscle activity events identified in operation ii) to determine a period activity value that represents a level of electrical activity of the patient during the selected time period; and
        iv) repeating operations i)-iii) for a second one of the time periods in the plurality of time periods; and
    d) displaying to a user a representation of the period activity value for the at least two time periods.

2. The method of claim 1 including transmitting data representing the acquired composite electrical waveform through the skin from the implanted medical device to a receiver module external to the body.

3. The method of claim 1 including providing a receiver module external to the body for receiving transmitted data from the medical device, the receiver module comprising a programming module storing programming information for the medical device.

4. The method of claim 1 including transmitting information about the period activity values through the skin from the implanted medical device to a receiver module external to the body.

5. The method of claim 1 including transmitting the acquired composite electrical waveform from a subcutaneous antenna implanted in the body.

6. The method of claim 1, wherein operation ii) further comprises high-pass filtering, rectifying, and smoothing of the acquired composite electrical waveform.

7. The method of claim 1, wherein operation ii) comprises comparing an amplitude of the frequency of the composite electrical waveform acquired during the selected time period to a threshold value.

8. The method of claim 7, wherein operation ii) further comprises comparing the acquired composite electrical waveform to at least one additional threshold value to identify non-cardiac muscle activity events in the acquired composite electrical waveform that occurred during the selected time period.

9. The method of claim 1, wherein operation iii) comprises counting the non-cardiac muscle activity events identified in operation ii).

10. The method of claim 1 including providing the period activity value being a function of an amplitude of each of the non-cardiac muscle activity events identified in operation ii).

11. The method of claim 1 including providing the period activity value being a function a duration of each of the non-cardiac muscle activity events identified in operation ii).

12. The method of claim 11, wherein, for each one of the plurality of time periods, the corresponding histogram represents in a first dimension a first period activity value based on a number of the non-cardiac muscle activity events identified in operation ii), and further represents in a second dimension a second period activity value based on an amplitude of each of the non-cardiac muscle activity events identified in operation ii).

13. The method of claim 11, wherein, for each one of the plurality of time periods, the corresponding histogram represents in a first dimension a first period activity value based on a number of the non-cardiac muscle activity events identified in operation ii), and further represents in a second dimension a second period activity value based on a duration of each of the non-cardiac muscle activity events identified in operation ii).

14. The method of claim 1 including providing the displayed representation comprising a histogram.

15. The method of claim 1 including providing the composite electrical waveform comprising the non-cardiac electrical signal as relatively high frequency signals superimposed on repeating cardiac electrical signal as relatively low frequency signals.

16. The method of claim 1 including displaying the non-cardiac electrical signals as an episode of relatively higher frequency signals superimposed on repeating cardiac electrical signals.

17. A method of presenting physical activity information for an individual by detecting non-cardiac muscle noise in electrocardiogram (ECG) waveform information collected by an implanted medical device, the method comprising the steps of:
  a) implanting a medical device within a patient, the medical device comprising at least a first subcutaneous electrode implanted in or adjacent to the patient's heart and a second subcutaneous electrode implanted in or adjacent to non-cardiac muscle or fascia tissue of the chest, abdomen, back or neck regions of the patient;
  b) acquiring electrical waveforms from the first and second subcutaneous electrodes, the electrical waveforms comprising electrical activity signals generated by cardiac activity of the heart and non-cardiac electrical activity signals including both psychological and physiological data generated by the muscle or fascia tissue of the patient during each of a plurality of non-overlapping time periods;
  c) post-processing at least two of the acquired electrical waveforms of the cardiac electrical activity signals and of the non-cardiac electrical activity signals by performing the following operations:
    i) selecting one of the plurality of non-overlapping time periods;
    ii) identifying non-cardiac muscle activity events in the acquired electrical waveforms that occurred during the selected time period;
    iii) aggregating the non-cardiac muscle activity events identified in operation ii) to determine a period activity value that represents a level of electrical activity of the patient during the selected time period; and
    iv) repeating operations i)-iii) for a second one of the time periods in the plurality of time periods; and
  d) displaying to a user a representation of the period activity value for the at least two time periods.

* * * * *

UNITED STATES PATENT AND TRADEMARK OFFICE
CERTIFICATE OF CORRECTION

| | | |
|---|---|---|
| PATENT NO. | : 8,180,442 B2 | Page 1 of 1 |
| APPLICATION NO. | : 11/956884 | |
| DATED | : May 15, 2012 | |
| INVENTOR(S) | : Andres Belalcazar and Ji Chen | |

It is certified that error appears in the above-identified patent and that said Letters Patent is hereby corrected as shown below:

Column 22, line 48, claim 11 "function a duration" should be "function of a duration"

Signed and Sealed this
Eighteenth Day of September, 2012

David J. Kappos
*Director of the United States Patent and Trademark Office*